(12) United States Patent
Goel et al.

(10) Patent No.: US 10,260,105 B2
(45) Date of Patent: Apr. 16, 2019

(54) MIR-320E AND COLORECTAL CANCER

(71) Applicant: BAYLOR RESEARCH INSTITUTE, Dallas, TX (US)

(72) Inventors: Ajay Goel, Dallas, TX (US); Lucia Perez-Carbonell, Dallas, TX (US); C. Richard Boland, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 15/120,052

(22) PCT Filed: Feb. 18, 2015

(86) PCT No.: PCT/US2015/016285
§ 371 (c)(1),
(2) Date: Aug. 18, 2016

(87) PCT Pub. No.: WO2015/126886
PCT Pub. Date: Aug. 27, 2015

(65) Prior Publication Data
US 2017/0067115 A1    Mar. 9, 2017

Related U.S. Application Data

(60) Provisional application No. 61/941,340, filed on Feb. 18, 2014.

(51) Int. Cl.
| | | |
|---|---|---|
| *C12Q 1/68* | (2018.01) | |
| *A61K 31/513* | (2006.01) | |
| *C12N 15/113* | (2010.01) | |
| *G06F 19/00* | (2018.01) | |
| *C12Q 1/6886* | (2018.01) | |
| *G16H 40/63* | (2018.01) | |
| *G16H 10/60* | (2018.01) | |

(52) U.S. Cl.
CPC .......... *C12Q 1/6886* (2013.01); *A61K 31/513* (2013.01); *C12N 15/113* (2013.01); *G06F 19/00* (2013.01); *G16H 10/60* (2018.01); *G16H 40/63* (2018.01); *C12N 2310/14* (2013.01); *C12N 2320/30* (2013.01); *C12Q 2600/118* (2013.01); *C12Q 2600/158* (2013.01); *C12Q 2600/178* (2013.01); *Y02A 90/22* (2018.01); *Y02A 90/26* (2018.01)

(58) Field of Classification Search
None
See application file for complete search history.

(56) References Cited

U.S. PATENT DOCUMENTS

| | | | | |
|---|---|---|---|---|
| 2009/0075258 A1 | 3/2009 | Latham | | 435/6 |
| 2010/0113577 A1 | 5/2010 | Shi | | 514/44 |
| 2010/0167940 A1 | 7/2010 | Feinberg | | 506/7 |
| 2010/0184046 A1 | 7/2010 | Klass et al. | | 435/7.1 |
| 2010/0197774 A1 | 8/2010 | Croce | | 435/6 |
| 2010/0298151 A1 | 11/2010 | Taylor et al. | | 435/6 |
| 2011/0171646 A1 | 7/2011 | Schmittgen et al. | | 435/6.11 |
| 2011/0251098 A1 | 10/2011 | Showe et al. | | 536/23.1 |
| 2012/0065098 A1 | 3/2012 | Croce et al. | | 435/6 |
| 2013/0142728 A1* | 6/2013 | Beaudenon-Huibregtse | | C12Q 1/6886 424/1.11 |
| 2014/0120545 A1* | 5/2014 | Umansky | | C12Q 1/6883 435/6.12 |

FOREIGN PATENT DOCUMENTS

| | | |
|---|---|---|
| WO | WO 2009/140670 | 11/2009 |
| WO | WO 2012/048236 | 4/2012 |
| WO | WO 2012/119051 | 9/2012 |
| WO | WO 2013/093635 | 6/2013 |
| WO | WO 2013/095956 | 6/2013 |
| WO | WO 2013/096888 | 6/2013 |

OTHER PUBLICATIONS

Schetter et al (JAMA, Jan. 30, 2008, 299(4): 425-436).*
Liu et al (Nature Protocaols 3(4): 563-578).*
Xiong et al (Computers in BiologyandMedicine 43:1252-1260, 2013).*
Liu et al (J. Genet. Genomics 37 (2010) 347-358) (Year: 2010).*
Motoyama et al (Int. J. oncol. 34: 1069-1075, 2009) (Year: 2009).*
Willett et al (Clin Cancer Res 2007;13(22 Suppl) Nov. 15, 2007) (Year: 2007).*
Costi et al (Ann Surg Oncol (2010) 17:432-440) (Year: 2010).*
Alberts et al. *Jama.* 307:1383-93, 2012.
Amado, et al., "Wild-type KRAS is required for panitumumab efficacy in patients with metastatic colorectal cancer", J Clin Oncol. 2008; 26:1626-34.
Bandres, et al., "Identification by Real-time PCT of 13 mature microRNAs differentially expressed in colorectal cancer and non-tumoral tissues," Molecular Cancer 2006, 5:29.
Bohanes, et al., "A review of excision repair cross-complementation group 1 in colorectal cancer", Clin Colorectal Cancer. 2011;10:157-64.
Boland and Goel "Microsatellite instability in colorectal cancer", Gastroenterology. 2010; 138:2007-87 e3.

(Continued)

*Primary Examiner* — Richard A Schnizer
(74) *Attorney, Agent, or Firm* — Norton Rose Fulbright US LLP

(57) ABSTRACT

Embodiments provide methods and compositions related to determining treatments for colorectal cancer patients by detection and analysis of the expression level of miRNA such as miR-320e in the patients. Embodiments provide predictive, prognostic and/or diagnostics methods by identifying miRNAs that are useful for clinical management of cancer patients, particularly colorectal cancer patients or patients at risk or determined to have colorectal cancer. Methods and compositions are based, in part, on the discovery that expression of certain miRNAs in cancer patients is associated with advancing cancer stages and/or can predict the responsiveness of cancer therapy, and can, therefore, provide basis for designing treatment strategies. In particular embodiments, the miRNA molecule is miR-320, particularly miR-320e.

17 Claims, 7 Drawing Sheets

Specification includes a Sequence Listing.

(56) References Cited

OTHER PUBLICATIONS

Calin and Croce "MicroRNA signatures in human cancers", Nat Rev Cancer. 2006;6:857-66.
Chen Y. et al., "Altered expression of MiR-148a and MiR-152 in gastrointestinal cancers and its clinical significance." J Gastrointest Surg. Jul. 2010;14(7):1170-9.
Duursma, et al., "miR-148 targets human DNMT3b protein coding region," RNA 2008;14:872-7.
Fujita et al., "MiR-148a attenuates paclitaxel resistance of hormone-refractory, drug-resistant prostate cancer PC3 cells by regulating MSK1 expression." J Biol Chem. Jun. 18, 2010;285(25):19076-84.
Garzon, et al., "MicroRNAs in Cancer", Annu Rev Med. 2009;60:167-79.
Hummel, et al., "Mir-148a improves response to chemotherapy in sensitive and resistant oesophageal adenocarcinoma and squamous cell carcinoma cells." J Gastrointest Surg. Mar. 2011;15(3):429-38. doi: 10.1007/s11605-011-1418-9. Epub Jan. 19, 2011.
International Search Report and Written Opinion for Application No. PCT/US2012/068591 dated Feb. 22, 2012.
International Search Report and Written Opinion issued for Application No. PCT/US2015/016285 dated Jun. 2, 2015.
Jemal, et al., "Cancer statistics, 2010", CA Cancer J Clin. 2010;60:277-300.
Jover, et al., "5-Fluorouracil adjuvant chemotherapy does not increase survival in patients with CpG island methylator phenotype colorectal cancer", Gastroenterology. 2011;140:117481.
Kalimutho, et al., "Epigenetically silenced miR-34b/c as a novel faecal-based screening marker for colorectal cancer," Br J Cancer. May 24, 2011; 104(11): 1770-1778.
Karapetis, et al., "K-ras mutations and benefit from cetuximab in advanced colorectal cancer" N Engl J Med, 2008; 359:1757-65.
Koopman, et al., "A review on the use of molecular markers of cytotoxic therapy for colorectal cancer, what have we learned?" Eur J Cancer. 2009;45:1935-49.
Langer, et al., "High BAALC expression associates with other molecular prognostic markers, poor outcome, and a distinct gene-expression signature in cytogenetically normal patients younger than 60 years with acute myeloid leukemia: a Cancer and Leukemia Group B (CALGB) study", Blood. 2008;111:5371-9.
Lehmann, et al., "Epigenetic inactivation of microRNA gene hsa-mir-9-1 in human breast cancer", J Pathol. 2008;214(1):17-24.
Liffers, et al., "MicroRNA-148a is down-regulated in human pancreatic ductal adenocarcinomas and regulates cell survival by targeting CDC25B", Laboratory Investigation 2011;91:1472-9.
Lujambio, et al., "A microRNA DNA methylation signature for human cancer metastasis", Proc Natl Acad Sci U S A. 2008;105:13556-61.
Michael, et al., "Reduced accumulation of specific microRNAs in colorectal neoplasia", Mal Cancer Res. 2003;1:882-91.
Nugent et al "MicroRNA in colorectal cancer: Function, dysregulation and potential as novel biomarkers" European Journal of Surgical Oncology, 2011, 37: 649-654.
Pan, et al., "MicroRNA-21 and microRNA-148a contribute to DNA hypomethylation in lupus CD4+ T cells by directly and indirectly targeting DNA methyltransferase 1", J Immunol. 2010;184:6773-81.
Perez-Carbonell et al. "MiR-320e is a Prognostic and Predictive Biomarker in Colorectal Cancer," Gastroenterology, 2014, AGA Abstract #110, 146(5, Suppl 1): S-30. Entire Document.
Ribic, et al., "Tumor microsatellite-instability status as a predictor of benefit from fluorouracil-based adjuvant chemotherapy for colon cancer", N Engl J Med. 2003;349:247-57.
Sargent, et al., "Defective mismatch repair as a predictive marker for lack of efficacy of fluorouracil-based adjuvant therapy in colon cancer", J Clin Oncol. 2010; 28:3219-26.
Schepeler, et al., "Diagnostic and prognostic microRNAs in stage II colon cancer", Cancer Res. 2008;68:6416-24.
Schetter, et al., "MicroRNA expression profiles associated with prognosis and therapeutic outcome in colon adenocarcinoma", JAMA. 2008;299:425-36.
Sinicrope, et al., "DNA mismatch repair status and colon cancer recurrence and survival in clinical trials of 5-fluorouracil-based adjuvant therapy," J Natl Cancer Inst. 2011;103:863-75.
Takagi, et al., "Post-transcriptional regulation of human pregnane X receptor by micro-RNA affects the expression of cytochrome P450 3A4", J Biol Chem. 2008;283:9674-80.
Takahashi, et al., "Mir-148a Expression Status Predicts Clinical Outcome in Patients With Advanced Colorectal Cancer," Gastroenterology 2012, vol. 142, Issue 5, Supplement 1, pp. S-185-S-186.
Takahashi, et al., "The Clinical Significance of MiR-148a as a Predictive Biomarker in Patients with Advanced Colorectal Cancer" PLoS ONE 7(10): e46684. doi:10.1371/journal.pone.0046684, (2012).
Therasse, et al., "New guidelines to evaluate the response to treatment in solid tumors. European Organization for Research and Treatment of Cancer, National Cancer Institute of the United States, National Cancer Institute of Canada", J Natl Cancer Inst. 2000;92:205-16.
Toyota, et al., "Epigenetic silencing of microRNA-34b/c and B-cell translocation gene 4 is associated with CpG island methylation in colorectal cancer", Cancer Res. 2008;68:4123-32.
Van Schaeybroeck, et al., "Implementing prognostic and predictive biomarkers in CRC clinical trials", Nat Rev Clin Oncol. 2011;8:222-32.
Vilar, and Gruber "Microsatellite instability in colorectal cancer—the stable evidence", Nat Rev Clin Oncol. 2010; 7:153-62.
Zhang, et al., "MiR-148a promotes apoptosis by targeting Bcl-2 in colorectal cancer," Cell Death Differ. Nov. 2011; 18(11): 1702-1710.
Zheng, et al., "MicroRNA-148a Suppresses Tumor Cell Invasion and Metastasis by Downregulating ROCK1 in Gastric Cancer", Clin Cancer Res. Dec. 15, 2011; 17(24):7574-83.
Berger et al., "Thymidylate synthase as a chemotherapeutic drug target: Where are we after fifty years?" Cancer Biology & Therapy, 5(9): 2006, 1238-1241.
Extended European Search Report issued in European Application No. 15752265.7, dated Sep. 8, 2017.
Hur et al., "Su1880: Identification of a novel metastasis-specific miRNA signature in human colorectal cancer," Gastroenterology, 142(5): 2012, S-525.
Jia et al., "Plasma miR-17-5p, miR-20a and miR-22 are down-regulated in women with endometriosis," Human Reproduction, 28(2): 2013, 322-330.
Salendo et al., "Identification of a microRNA expression signature for chemoradiosensitivity of colorectal cancer cells, involving miRNAs-320a, -224, -132 and let7g," Radiotherapy and Oncology, 108(3): 2013, 451-457.

* cited by examiner

SEQUENCE LISTING

```
<160> NUMBER OF SEQ ID NOS: 1

<210> SEQ ID NO 1
<211> LENGTH: 18
<212> TYPE: RNA
<213> ORGANISM: Artificial Sequence
<220> FEATURE:
<223> OTHER INFORMATION: Synthetic Primer

<400> SEQUENCE: 1
aaagcugggu ugagaagg                                               18
```

MIR-320E AND COLORECTAL CANCER

This application in a national phase application under 35 U.S.C. § 371 of International Application No. PCT/US2015/016285, filed Feb. 18, 2015, which claims the benefit of priority to U.S. Provisional Patent Application Ser. No. 61/941,340, filed Feb. 18, 2014, the entire contents of each of which are hereby incorporated by reference in their entirety.

The invention was made with government support under Grant No. K05CA-142885 awarded by the National Institutes of Health. The government has certain rights in the invention.

BACKGROUND OF THE INVENTION

1. Field of the Invention

The present invention relates generally to the fields of molecular biology and oncology. More particularly, it concerns methods and compositions involving microRNA (miRNAs) molecules and cancer prognosis and treatment.

2. Description of Related Art

Currently, colorectal cancer (CRC) patients with lymph node metastasis (TNM stage III) are treated with adjuvant chemotherapy that includes cytotoxic drugs such as 5-fluorouracil (5-FU) and oxaliplatin, following surgical resection of the cancer. Similarly, patients with distant metastatic CRC (stage IV) are treated with various combinations of chemotherapeutic drugs and molecularly-targeted drugs that include anti-VEGF and anti-EGFR antibodies. Although these treatment regimens have improved outcomes in patients with advanced CRC, a significant proportion of individuals fail to derive any benefit from such treatments, and some experience worse outcomes as a result of drug-associated toxicities.

Thus, there is a need for developing predictive biomarkers that can select the subgroup of patients that will benefit from conventional chemotherapeutic drugs, so that patients who will not benefit from the treatment can be spared from drug toxicity and offered alternate treatments.

SUMMARY OF THE INVENTION

Embodiments provide predictive, prognostic and/or diagnostics methods by identifying miRNAs that are useful for clinical management of cancer patients, particularly colorectal cancer patients or patients at risk or determined to have colorectal cancer. Methods and compositions are based, in part, on the discovery that expression of certain miRNAs in cancer patients is associated with advancing cancer stages and/or can predict the responsiveness of cancer therapy, and can, therefore, provide basis for designing treatment strategies. In particular embodiments, the miRNA molecule is miR-320, particularly miR-320e. In some embodiments the miR-320 is a human sequence (hsa-miR-320e), and it may have a sequence as set forth in 5'-aaagcugggguugagaagg-3' (SEQ ID NO:1) or having at least or at most 70, 80, 90, 91, 92, 93, 94, 95, or 100% sequence identity with SEQ ID NO:1, or any value or range derivable therefrom.

Thus, there may be first provided a method for treating colorectal cancer in a patient. In particular aspects, the cancer is stage I, II or III colorectal cancer. In further aspects, the cancer is stage IV colorectal cancer or a metastatic cancer. The method may comprise administering a treatment comprising a thymidylate synthase inhibitor to a patient that is determined to have a decreased expression level in a gene encoding an miRNA molecule compared to a control or reference expression level. In further embodiments, the method comprises administering a treatment other than a thymidylate synthase inhibitor to a patient that is determined not to have a decreased expression level in a gene encoding an miRNA molecule compared to a control or reference expression level. In particular embodiments, the miRNA molecule is miR-320, particularly miR-320e. In additional embodiments, the patient may be under a current colorectal cancer treatment comprising a thymidylate synthase inhibitor or administered a prior colorectal cancer treatment comprising a thymidylate synthase inhibitor.

In certain embodiments there is a method for treating colorectal cancer in a patient, the method comprising: administering a treatment comprising a thymidylate synthase inhibitor to a patient that is determined to have a decreased expression level of miR-320e relative to the expression level of miR-320e in recurrent colorectal cancer or administering a cancer treatment other than the thymidylate synthase inhibitor to a patient determined to have an increased expression level of miR-320e relative to the expression level of miR-320e in recurrent colorectal cancer. The expression level of miR-320e in the patient may be compared directly or indirectly to the level of expression in a recurrent colorectal cancer patient in order to determine if the expression level of the patient is increased or decreased. In some embodiments, a patient who is at risk or increased risk for recurrent colorectal cancer is administered a cancer treatment other than a thymidylate synthase inhibitor such as 5-FU. In other embodiments, a patient who is not considered at risk or who is considered to have a lower risk for recurrent colorectal cancer is administered a cancer treatment that includes a thymidylate synthase inhibitor such as 5-FU.

In particular embodiments, the treatment comprising a thymidylate synthase inhibitor also comprises cytotoxic agents such as a pyrimidine analog and/or a platinum-based antineoplastic, e.g., a 5-fluorouracil (5-FU) and/or oxaliplatin.

In certain embodiments, the method may comprise identifying a patient that has an increased expression level in a gene encoding an miRNA molecule as compared to a control or reference expression level. Because the high expression level of the particular miR-320e level indicates low responsiveness of the particular subject to the traditional fluorouracil (5-FU) chemotherapy, the subject having a high miR-320e level may be prescribed a treatment that is a non-5-FU therapy or an alternative treatment.

For example, a non-5-FU therapy or an alternative treatment is a different chemotherapy that is not based on a thymidylate synthase inhibitor or a different chemotherapy such as any chemotherapy other than 5-FU; or different non-chemotherapy cancer therapy, such as radiation therapy or immunotherapy, or a method for lowering the expression of the particular miRNA expression level, such as an miRNA-320e inhibitor, which may be a small molecule or an inhibitory RNA.

In other embodiments, the patient that may be identified as having a low expression level of miR-320e as compared to a control may be administered a traditional chemotherapy comprising, for example, anti-metabolites like a thymidylate synthase inhibitor. The thymidylate synthase inhibitor may be a pyrimidine analog, particularly fluorouracil (5-FU), optionally in combination with or a platinum-based antineoplastic. The platinum-based antineoplastic may be Oxaliplatin. A traditional chemotherapy for colorectal cancer may also comprise inhibitors for growth factors, such as Avastin® (bevacizumab) and epidermal growth factor receptor Erbitux®(cetuximab).

Methods may also be provided for evaluating the response of a colorectal cancer patient to a colorectal cancer treatment. The method may comprise determining in a sample from a patient under or after a colorectal cancer treatment that the sample has increased expression levels in a gene encoding miR-320e compared to a control or reference expression level for the gene. For example, the increased expression indicates that the patient's poor prognosis or risk of poor response to the treatment as compared to a control. The method may further comprise identifying the patient with the increased expression as being at risk for poor response to the colorectal cancer treatment or having poor prognosis. The method may still further comprise calculating a prognosis or response score for the patient based on the miR-320e expression level. In further embodiments, the method may further comprise monitoring the patient for colorectal cancer recurrence or prescribing a different cancer treatment.

In other embodiments, the method may comprise determining that the sample does not have increased expression levels or, alternatively, has decreased expression levels in the gene. Because the expression level is correlated with the response or prognosis, the method may further comprise identifying the patient not having the increased expression or, alternatively, having decreased expression levels as likely being responsive to the treatment or having good prognosis.

There may be provided a method of treating a patient with colorectal cancer, comprising identifying the patient as having an increased expression level in a gene encoding miR-320e compared to a control or reference expression level for the gene; and administering a treatment that inhibits or reduces the expression level of the miR-320e gene, such as an siRNA that specifically binds miR-320e.

In further embodiments, the method may comprise determining the expression level of the miRNA molecule. In still further embodiments, the method may comprise obtaining a sample of the subject or patient or obtaining a sample from the subject or patient. Non-limiting examples of the sample include a tissue sample, a whole blood sample, a urine sample, a saliva sample, a serum sample or a fecal sample. In particular embodiments, the sample is a rectum sample, a colon sample or a cecum sample.

The methods of obtaining a sample provided herein include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from rectal, cecum, or colon tissue by any of the biopsy methods previously mentioned. In other embodiments the sample may be obtained from any of the tissues provided herein that include but, are not limited to, gall bladder, skin, heart, lung, breast, pancreas, liver, muscle, kidney, smooth muscle, bladder, intestine, brain, prostate, esophagus, or thyroid tissue.

Alternatively, the sample may include, but not be limited to, blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample. In particular embodiments, the sample may be a bodily fluid sample, including, but not limited to, a whole blood sample, a urine sample, a saliva sample, a tear sample, a serum sample, or a plasma sample. In further embodiments, the sample may be a sample that has been enriched for certain exosomes.

In certain aspects the sample is obtained from cystic fluid or fluid derived from a tumor or neoplasm. In yet other embodiments the cyst, tumor or neoplasm is in the digestive system. In certain aspects of the current systems, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include, but are not limited to: glycerol, ethylene glycol, sucrose, or glucose.

Some embodiments further involve isolating nucleic acids such as ribonucleic or RNA from a biological sample or in a sample of the patient. In certain aspects, isolating nucleic acids may not be needed or may be avoided. Other steps may or may not include amplifying a nucleic acid in a sample and/or hybridizing one or more probes to an amplified or non-amplified nucleic acid.

In further aspects, the method may comprise assaying nucleic acids in exosomes. For example, exosomes positive for a cancer-specific antigen may be isolated from a sample such as a circulating sample, particularly a blood sample or a serum sample or any bodily fluid sample. The method may further comprise determining miRNA expression level, such as miR-320e, in the exosomes. In certain aspects, there may be provided a method comprising isolating or enriching exosomes, particularly exosomes in a particular cancer, such as colorectal cancer, and determining the miR-320 expression in the exosomes. The isolation or enrichment of exosomes may involve the use of an antibody that binds to a target expressed in exosomes, such as A33.

In certain aspects, the method may further comprise normalizing the expression level of miR-320e to a reference level of a different genetic marker, such as the expression level of hsa-miR-16, hsa-miR-26b, hsa-miR-92, hsa-miR-92N, hsa-miR-423, hsa-miR-374 and hsa-miR-16, RNU24, RNU66, RNU19, RNU38B, RNU49, Z30, RNU48, RNU43, U18, RNU58B, RNU58A, RPL21, U54, HY3, U75, RNU68, RNU44, U47 and RNU6B, or any markers that can be used as an internal standard. An ideal internal standard may be expressed at a constant level among different tissues, and may be unaffected by the experimental treatment. In the particular embodiment, the expression level of miR-320e may be normalized by the expression level of another miRNA, such as hsa-miR-16. In other embodiments, expression levels may be compared to an expression level that varies with the sample or disease state; that is, to an expression level that is not unchanged or is a normalizing expression level.

The methods may further comprise assaying nucleic acids in a sample. In certain embodiments, a microarray or any methods known in the art may be used to measure or assay the level of miRNA expression in a sample. The nucleic acid assay methods may further include, but not be limited to, PCR, digital PCR, dd PCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seq (Tagged-Amplicon deep sequencing), PAP (Pyrophosphorolysis-activation polymerization), RT-PCR, in situ hybridization, northern hybridization, hybridization protection assay (HPA)(Gen-Probe), branched DNA (bDNA) assay (Chiron), rolling circle amplification (RCA), single molecule hybridization detection (US Genomics), Invader assay (ThirdWave Technologies), and/or Bridge Ligation Assay (Genaco), next generation RNA sequencing, or a combination thereof. The methods may further comprise recording the miRNA expression level in a tangible medium or reporting the expression level to the patient, a health care payer, a physician, an insurance agent, or an electronic system.

In some embodiments, methods will involve determining or calculating a prognosis score based on data concerning the expression level of the miRNA, meaning that the expression level of the miRNA is at least one of the factors on which the score is based. A prognosis score, which may include a response score, may provide information about the patient, such as the general probability whether the patient is sensitive to a particular therapy or has poor survival or high chances of recurrence. In certain embodiments, a prognosis value is expressed as a numerical integer or number that represents a probability of 0% likelihood to 100% likelihood that a patient has a chance of poor survival or cancer recurrence or poor response to a particular treatment.

In some embodiments, the prognosis or response score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a chance of poor survival or cancer recurrence or poor response to a particular treatment. Alternatively, the probability may be expressed generally in percentiles, quartiles, or deciles.

In further aspects, the expression level or score may be a relative expression level or score based on comparison with a certain cutoff value or reference level, for example, as expressed in percentiles, quartiles, or deciles, such as 25, 50, 75 percentiles, or any range or value derivable therefrom. In particular aspects, the increase or decrease may be an increase from the $25^{th}$ percentile to the $75^{th}$ percentile, the $25^{th}$ percentile to the $50^{th}$ percentile, or the $50^{th}$ percentile to the $75^{th}$ percentile of the miR-320e distribution or vice versa, or any change based on a comparison between the patient and a median of a control group.

In certain aspects, the prognosis or response score may be calculated from or based on a hazard ratio. A hazard ratio may be the ratio of the hazard rates corresponding to the conditions described by two levels of an explanatory variable: for example, a hazard ratio may be a ratio of the hazard or chance of events (poor therapeutic response, recurrence, or poor survival or death) occurring after the treatment as compared with a control.

There may be provided methods for assigning weight to certain expression level or coefficients based on the expression level. A difference between or among weighted coefficients or expression levels of different genes, or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs), including expression levels in a gene encoding miR-320e.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression level of a gene encoding miR-320e in a sample from a patient; and b) determining a difference value in the expression levels using the information corresponding to the expression levels in the sample compared to a control or reference expression level for the gene.

In other aspects, tangible computer-readable medium further comprise computer-readable code that, when executed by a computer, causes the computer to perform one or more additional operations comprising making recommendations comprising: wherein the patient in the step a) is under or after a first treatment for colorectal cancer, administering the same treatment as the first treatment to the patient if the patient does not have an increased expression level of miR-320e; administering a different treatment from the first treatment to the patient if the patient has an increased expression level of miR-320e.

In some embodiments, receiving information comprises receiving from a tangible data storage device information corresponding to the expression levels from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a traditional colorectal therapy if the patient does not have an increased expression level of miR-320e, and/or or treating the patient with an alternative colorectal therapy if the patient has an increased expression level of miR-320e.

The tangible, computer-readable medium further comprise computer-readable code that, when executed by a computer, causes the computer to perform one or more additional operations comprising calculating a prognosis score for the patient. The operations may further comprise making recommendations comprising: administering a treatment comprising a thymidylate synthase inhibitor to a patient that is determined to have a decreased expression level. A method for determining the risk of recurrence in a patient who has or had colorectal cancer comprising: measuring an expression level of miR-320e in a biological sample from a patient; comparing the expression level of miR-320e in the biological sample to a control or reference sample that indicates whether the expression level is decreased compared to a level of expression in a sample that has a high risk of colorectal cancer recurrence; and, identifying the patient as not having a high risk of colorectal cancer recurrence if the expression level is decreased or identifying the patient as having a high risk of colorectal cancer recurrence if the expression level is similar or greater than the level of expression in the sample that has a high risk of colorectal cancer recurrence. Also provided are kits containing the disclosed compositions or compositions used to implement the disclosed methods. In some embodiments, kits can be used to evaluate one or more miRNA molecules or markers, including miR-320e and/or one or more normalizing miRNA molecules or other markers. In certain embodiments, a kit contains, contains at least, or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, or any range and combination derivable therein, miRNA probes or primers including those that may specifically hybridize under stringent conditions to miRNAs disclosed herein. In other embodiments, kits or methods may involve 1, 2, or more probes or primers, which may be capable of specifically detecting any biomarkers for expression.

Also included may be enzymes suitable for amplifying nucleic acids including various polymerases (RT, Taq, Seguenase™ etc.), deoxynucleotides and buffers to provide the necessary reaction mixture for amplification. Such kits also generally will comprise, in suitable means, distinct containers for each individual reagent and enzyme as well as for each primer or probe.

The kits may further comprise instructions for using the kit for assessing expression, means for converting the expression data into expression values and/or means or medians for analyzing the expression values to generate scores that predict response, diagnosis, survival, prognosis or indicate recommendations for treatment choices. Possible means for converting the expression data into expression values and/or means or medians and for analyzing the expression values and/or means or medians to generate scores that predict response, diagnosis, survival or prognosis or indicate recommendations for treatment choices may also be included.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Introduction

Figure 1A:
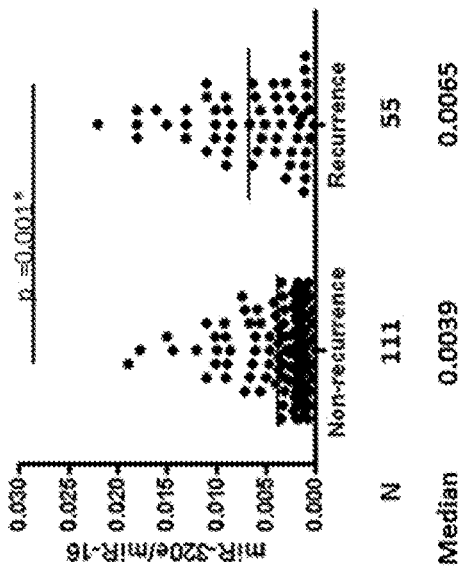
FIG. 1A-1E—MiR-320e expression in colonic mucosa from healthy individuals and CRC tissues from patients. miR320e results were expressed as $2^{-\Delta Ct}$ and normalized to miR-16. A. Colonic mucosa vs primary tumors—stage II-IV, miR-320e expression in colonic mucosa from healthy controls (NC), and in stage II, III and IV CRCs; the number of patients (N) and median expression (median) are listed below the graph. B. Recurrence vs Non-Recurrence—Stage II & III, recurrence during follow-up according to miR-320e expression in stage II & III CRC patients. C. Recurrence vs Non-Recurrence—stage II. Stage II CRC patients treated with 5-FU therapy and D. Recurrence vs Non-Recurrence—stage III. Stage III CRC patients treated with 5-FU therapy. E. Lymph nodes affected—stage MM. Number of nearby lymph nodes affected (N0=0, N1=0-4, N2>4) according to miR-320e expression.

Certain aspects provide a test that could assist physicians to select the optimal treatment strategy such as a chemotherapy for a patient from several alternative treatment options. A major clinical challenge in cancer treatment is to identify the subset of patients who will benefit from chemotherapy, both in metastatic and adjuvant settings. The number of anti-cancer drugs and multi-drug combinations has increased substantially in the past decade, however, treatments continue to be applied empirically using a trial-and-error approach. Clinical experience shows that some tumors are sensitive to several different types of chemotherapeutic agents, while other cancers of the same histology show selective sensitivity to certain drugs but resistance to others. Here methods and compositions are provided to determine the optimal treatment option for cancer patients.

II. Definitions

"Prognosis" refers to a prediction of how a patient will progress, and whether there is a chance of recovery. "Cancer prognosis" generally refers to a forecast or prediction of the probable course or outcome of the cancer, with or without a treatment. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. Prognosis may also include prediction of favorable responses to cancer treatments, such as a conventional cancer therapy. A response may be either a therapeutic response (sensitivity or recurrence-free survival) or a lack of therapeutic response (residual disease, which may indicate resistance or recurrence).

By "subject" or "patient" is meant any single subject for which therapy is desired, including an animal (for example a mammal), such as humans, non-human primates, rodents, dogs, pigs, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

As used herein, "increased expression" or "decreased expression" refers to an expression level of a biomarker in the subject's sample as compared to a reference level representing the same biomarker or a different biomarker. In certain aspects, the reference level may be a reference level of expression from a non-cancerous tissue from the same subject. Alternatively, the reference level may be a reference level of expression from a different subject or group of subjects, such as a reference level of expression from a subject or a group of subjects that have non-recurrent colorectal cancer, or from a subject or group that has at most 20, 30, 40, or 50% risk (or any range derivable therefrom) of having a recurrence of colorectal cancer. Alternatively, the reference level may be a reference level of expression from a subject or a group of subjects that has high recurrence risk, such as at least 50, 60, 70, 80, 90 or any range derivable therefrom of recurrence risk relative to a combined group of one or more non-recurrence subjects and recurrence subjects. The combined group may be randomly selected or may be a group of clinical trial subjects, subjects in a particular geographic area, an age group, a gender group, or a stage of colorectal cancer, or any group based on one or more classification criteria that does not include colorectal cancer recurrence. A person of ordinary skill in the art understands that an expression level from a test subject may be determined to have an elevated level of expression, a similar level of expression or a decreased level of expression compared to a reference level.

In further embodiments, the risk of recurrence can also be described as a risk of poor prognosis, risk of poor response to a particular therapy, or risk of death or metastasis.

In particular aspects, the reference level may be a value associated with a percentile, quartile, or decile or any statistic distribution values that represent low risk or high risk recurrence in a combined group.

For example, the reference level of expression may be an expression level obtained from a sample (e.g., a tissue, fluid or cell sample) of a subject or group of subjects without cancer, or an expression level obtained from a non-cancerous tissue of a subject or group of subjects with cancer, particularly colorectal cancer, or a subject or a group of subjects that have non-recurrence of colorectal cancer, or has at most 20, 30, 40, or 50% risk (or any range derivable therefrom) of recurrence of colorectal cancer. The control may be a control sample or control subject that may have non-recurrence of colorectal cancer, or have at most 20, 30, 40, or 50% risk (or any range derivable therefrom)of recurrence of colorectal cancer In certain aspects, "as compared to" includes indirect comparison to a reference level or a control that indicates non-recurrence or low recurrence risk by direct comparing with an increased level of expression or a control with high recurrence risk (at least 50, 60, 70, 80, 90 or any range derivable therefrom of recurrence risk) in a combined group described herein.

The reference level may be a single value or may be a range of values. The reference level of expression can be determined using any method known to those of ordinary skill in the art. In some embodiments, the reference level is an average level of expression determined from a cohort of subjects with cancer or without cancer. The reference level may also be depicted graphically as an area on a graph. In certain embodiments, a reference level is a normalized level, while in other embodiments, it may be a level that is not stable with respect to the tissue or biological sample being tested.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

III. MiRNA

Certain aspects are based, in part, on the systematic discovery and validation of prognostic/predictive miRNA(s) biomarkers in two independent clinical-based cohorts of CRC patients treated by a uniform 5-FU chemotherapy regimen. In certain embodiments, microRNAs (abbreviated miRNAs) may be used in methods and compositions for determining the prognosis, such as response to a particular cancer treatment, of a particular patient.

MiRNAs may be naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression.

There may be three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end.

The cleavage product, the premature miRNA (pre-miRNA) may be about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

MicroRNAs function by engaging in base pairing (perfect or imperfect) with specific sequences in their target genes' messages (mRNA). The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails.

MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis. Additionally, it is suggested that viral infection causes an increase in miRNAs targeted to silence "pro-cell survival" genes, and a decrease in miRNAs repressing genes associated with apoptosis (programmed cell death), thus tilting the balance toward gaining apoptosis signaling.

In other embodiments, there are synthetic nucleic acids that are miRNA inhibitors. An miRNA inhibitor is between about 17 to 25 nucleotides in length and comprises a 5' to 3' sequence that is at least 90% complementary to the 5' to 3' sequence of a mature miRNA. In certain embodiments, an miRNA inhibitor molecule is 17, 18, 19, 20, 21, 22, 23, 24, or 25 nucleotides in length, or any range derivable therein. Moreover, an miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. One of skill in the art could use a portion of the probe sequence that is complementary to the sequence of a mature miRNA as the sequence for an miRNA inhibitor. Moreover, that portion of the probe sequence can be altered so that it is still 90% complementary to the sequence of a mature miRNA.

In certain embodiments, a synthetic miRNA has one or more modified nucleic acid residues. In certain embodiments, the sugar modification is a 2'O-Me modification, a 2'F modification , a 2'H modification, a 2'amino modification, a 4'ribose modification, or a phosphorothioate modification on the carboxy group linked to the carbon at position 6. In further embodiments, there is one or more sugar modifications in the first or last 2 to 4 residues of the complementary region or the first or last 4 to 6 residues of the complementary region.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there is a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having an miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

Methods in certain aspects include reducing or eliminating activity of one or more miRNAs in a cell comprising introducing into a cell an miRNA inhibitor; or supplying or enhancing the activity of one or more miRNAs in a cell. Certain embodiments also concern inducing certain cellular characteristics by providing to a cell a particular nucleic acid, such as a specific synthetic miRNA molecule or a synthetic miRNA inhibitor molecule. However, in certain aspects of the methods, the miRNA molecule or miRNA inhibitor need not be synthetic. They may have a sequence that is identical to a naturally occurring miRNA or they may not have any design modifications. In certain embodiments, the miRNA molecule and/or an miRNA inhibitor are synthetic, as discussed above.

IV. Colorectal Cancer Staging and Treatments

Methods and compositions may be provided for treating colorectal cancer with particular applications of miRNA expression levels. Based on a profile of miRNA expression levels, for example, the miR320e, different treatments may be prescribed or recommended for different cancer patients.

A. Cancer Staging

Colorectal cancer, also known as colon cancer, rectal cancer, or bowel cancer, is a cancer from uncontrolled cell growth in the colon or rectum (parts of the large intestine), or in the appendix. Certain aspects of the methods are provided for patients that are stage II-IV colorectal cancer patients. In particular aspects, the patient is a stage IV patient.

The most common staging system is the TNM (for tumors/nodes/metastases) system, from the American Joint Committee on Cancer (AJCC). The TNM system assigns a number based on three categories. "T" denotes the degree of invasion of the intestinal wall, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome. Details of this system are in the graph below:

| AJCC stage | TNM stage | TNM stage criteria for colorectal cancer |
| --- | --- | --- |
| Stage 0 | Tis N0 M0 | Tis: Tumor confined to mucosa; cancer-in-situ |
| Stage I | T1 N0 M0 | T1: Tumor invades submucosa |
| Stage I | T2 N0 M0 | T2: Tumor invades muscularis propria |
| Stage II-A | T3 N0 M0 | T3: Tumor invades subserosa or beyond (without other organs involved) |
| Stage II-B | T4 N0 M0 | T4: Tumor invades adjacent organs or perforates the visceral peritoneum |
| Stage III-A | T1-2 N1 M0 | N1: Metastasis to 1 to 3 regional lymph nodes. T1 or T2. |
| Stage III-B | T3-4 N1 M0 | N1: Metastasis to 1 to 3 regional lymph nodes. T3 or T4. |
| Stage III-C | any T, N2 M0 | N2: Metastasis to 4 or more regional lymph nodes. Any T. |
| Stage IV | any T, any N, M1 | M1: Distant metastases present. Any T, any N. |

B. Traditional Therapy

For people with localized colorectal cancer, the preferred treatment is complete surgical removal with adequate margins, with the attempt of achieving a cure. This can either be done by an open laparotomy or sometimes laparoscopically. If there are only a few metastases in the liver or lungs they may also be removed. Sometimes chemotherapy is used before surgery to shrink the cancer before attempting to remove it. The two most common sites of recurrence of colorectal cancer is in the liver and lungs.

In both cancer of the colon and rectum, chemotherapy may be used in addition to surgery in certain cases. In rectal cancer, chemotherapy may be used in the neoadjuvant setting.

In certain embodiments, there may be a decision regarding whether traditional therapy or alternative treatment may be performed. Chemotherapy based on antimetabolites or thymidylate synthase inhibitors such as fluorouracil (5-FU) have been the main treatment for metastatic colorectal cancer and thus represents traditional therapy for colorectal cancer patients. Major progress has been made by the introduction of regimens containing new cytotoxic drugs, such as irinotecan or oxaliplatin. The combinations commonly used, e.g., irinotecan, fluorouracil, and Jeucovorin (FOLFIRI) and oxaliplatin, fluorouracil, and leucovorin (FOLFOX) can reach an objective response rate of about 50%. However, these new combinations remain inactive in one half of the patients and, in addition, resistance to treatment appear in almost all patients who were initially responders. More recently, two monoclonal antibodies targeting vascular endothelial growth factor Avastin® (bevacizumab) (Genentech Inc., South San Francisco Calif.) and epidermal growth factor receptor Erbitux®(cetuximab) (Imclone Inc. New York City) have been approved for treatment of metastatic colorectal cancer but are always used in combination with standard chemotherapy regimens. Thus, traditional therapy may include one or more of the chemical therapeutic agents including thymidylate synthase inhibitors or antimetabolites such as fluorouracil (5-FU), alone or in combination with other therapeutic agents. Any therapy for treating colorectal cancer that is not based on 5-FU may be alternative treatments.

For example, the first treatment to be tested for response or the traditional therapy may be antimetabolites or thymidylate synthase inhibitors, prodrugs, or salts thereof.

Antimetabolites can be used in cancer treatment, as they interfere with DNA production and therefore cell division and the growth of tumors. Because cancer cells spend more time dividing than other cells, inhibiting cell division harms tumor cells more than other cells. Anti-metabolites masquerade as a purine (azathioprine, mercaptopurine) or a pyrimidine, chemicals that become the building-blocks of DNA. They prevent these substances becoming incorporated in to DNA during the S phase (of the cell cycle), stopping normal development and division. They also affect RNA synthesis. However, because thymidine is used in DNA but not in RNA (where uracil is used instead), inhibition of thymidine synthesis via thymidylate synthase selectively inhibits DNA synthesis over RNA synthesis. Due to their efficiency, these drugs are the most widely used cytostatics. In the ATC system, they are classified under L01B.

Thymidylate synthase inhibitors are chemical agents which inhibit the enzyme thymidylate synthase and have potential as an anticancer chemotherapy. As an anti-cancer chemotherapy target, thymidylate synthetase can be inhibited by the thymidylate synthase inhibitors such as fluorinated pyrimidine fluorouracil, or certain folate analogues, the most notable one being raltitrexed (trade name Tomudex). Five agents were in clinical trials in 2002: raltitrexed, pemetrexed, nolatrexed, ZD9331, and GS7904L. Additional non-limiting examples include: Raltitrexed, used for colorectal cancer since 1998; Fluorouracil, used for colorectal cancer; BGC 945; OSI-7904L.

In further embodiments, there may be involved prodrugs that can be converted to thymidylate synthase inhibitors in the body, such as Capecitabine (INN), an orally-administered chemotherapeutic agent used in the treatment of numerous cancers. Capecitabine is a prodrug, that is enzymatically converted to 5-fluorouracil in the body.

If cancer has entered the lymph nodes, adding the chemotherapy agents fluorouracil or capecitabine increases life expectancy. If the lymph nodes do not contain cancer, the benefits of chemotherapy are controversial. If the cancer is widely metastatic or unresectable, treatment is then palliative. For example, a number of different chemotherapy medications may be used. Chemotherapy agents for this condition may include capecitabine, fluorouracil, irinotecan, leucovorin, oxaliplatin and UFT. Another type of agent that is sometimes used are the epidermal growth factor receptor inhibitors.

C. Alternative Treatments

In certain embodiments, alternative treatments may be prescribed or recommended based on the biomarker profile. In addition to traditional chemotherapy for colorectal cancer patients, cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

While a combination of radiation and chemotherapy may be useful for rectal cancer, its use in colon cancer is not routine due to the sensitivity of the bowels to radiation. Just as for chemotherapy, radiotherapy can be used in the neoadjuvant and adjuvant setting for some stages of rectal cancer. Thus, radiation may be considered alternative treatment when traditional chemotherapy alone does not work.

In people with incurable colorectal cancer, treatment options including palliative care can be considered for improving quality of life. Surgical options may include non-curative surgical removal of some of the cancer tissue, bypassing part of the intestines, or stent placement. These procedures can be considered to improve symptoms and reduce complications such as bleeding from the tumor, abdominal pain and intestinal obstruction. Non-operative methods of symptomatic treatment include radiation therapy to decrease tumor size as well as pain medications Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells. Many tumor markers exist and any of these may be suitable for targeting. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In yet another embodiment, the secondary treatment is a gene therapy. In certain embodiments, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It is further understood that the sequence includes the degenerate codons of the native sequence or sequences which may be introduced to provide codon preference in a specific host cell. Examples of tumor suppressor nucleic acids within this definition include, but are not limited to APC, CYLD, HIN-I, KRAS2b, p16, p19, p21, p27, p27mt, p53, p57, p73, PTEN, Rb, Uteroglobin, Skp2, BRCA-I, BRCA-2, CHK2, CDKN2A, DCC, DPC4, MADR2/JV18, MEN1, MEN2, MTS1, NF1, NF2, VHL, WRN, WT1, CFTR, C-CAM, CTS-I, zacl, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Other exemplary tumor suppressor genes are described in a database of tumor suppressor genes at world wide web through www.cise.ufl.edu/~yyl/HTML-TSGDB/Homepage.litml. This database is herein specifically incorporated by reference into this and all other sections of the present application. Nucleic acids encoding tumor suppressor genes, as discussed above, include tumor suppressor genes, or nucleic acids derived therefrom {e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied.

D. Monitoring

In certain aspects, the biomarker-based method may be combined with one or more other colon cancer diagnosis or screening tests at increased frequency if the patient is determined to be at high risk for recurrence or have a poor prognosis based on the biomarker described above.

The colon monitoring may include any methods known in the art. In particular, the monitoring include obtaining a sample and testing the sample for diagnosis. For example, the colon monitoring may include colonoscopy, which is the endoscopic examination of the large bowel and the distal part of the small bowel with a CCD camera or a fiber optic camera on a flexible tube passed through the anus. It can provide a visual diagnosis (e.g. ulceration, polyps) and grants the opportunity for biopsy or removal of suspected colorectal cancer lesions. Thus, colonoscopy or coloscopy can be used for treatment.

In further aspects, the monitoring diagnosis may include sigmoidoscopy, which is similar to colonoscopy—the difference being related to which parts of the colon each can examine. A colonoscopy allows an examination of the entire colon (1200-1500 mm in length). A sigmoidoscopy allows an examination of the distal portion (about 600 mm) of the colon, which may be sufficient because benefits to cancer survival of colonoscopy have been limited to the detection of lesions in the distal portion of the colon. A sigmoidoscopy is often used as a screening procedure for a full colonoscopy, often done in conjunction with a fecal occult blood test (FOBT). About 5% of these screened patients are referred to colonoscopy.

In additional aspects, the monitoring diagnosis may include virtual colonoscopy, which uses 2D and 3D imagery reconstructed from computed tomography (CT) scans or from nuclear magnetic resonance (MR) scans, as a totally non-invasive medical test.

The monitoring include the use of one or more screening tests for colon cancer including, but not limited to fecal occult blood testing, flexible sigmoidoscopy and colonoscopy. Of the three, only sigmoidoscopy cannot screen the right side of the colon where 42% of malignancies are found. Virtual colonoscopy via a CT scan appears as good as standard colonoscopy for detecting cancers and large adenomas but is expensive, associated with radiation exposure, and cannot remove any detected abnormal growths like standard colonoscopy can. Fecal occult blood testing (FOBT) of the stool is typically recommended every two years and can be either guaiac based or immunochemical. Annual FOBT screening results in a 16% relative risk reduction in colorectal cancer mortality, but no difference in all-cause mortality. The M2-PK test identifies an enzyme in colorectal cancers and polyps rather than blood in the stool. It does not require any special preparation prior to testing. M2-PK is sensitive for colorectal cancer and polyps and is able to detect bleeding and non-bleeding colorectal cancer and polyps. In the event of a positive result people would be asked to undergo further examination e.g. colonoscopy.

V. Sample Preparation

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from colorectal tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is colorectal. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example colon) and one or more samples from another tissue (for example buccal) may be obtained for diagnosis by the methods. In some cases, multiple samples such as one or more samples from one tissue type (e.g. rectal) and one or more samples from another tissue (e.g. cecum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments, of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

VI. Nucleic Acid Assays

Aspects of the methods include assaying nucleic acids to determine expression levels. Arrays can be used to detect differences between two samples. Specifically contemplated applications include identifying and/or quantifying differences between miRNA from a sample that is normal and from a sample that is not normal, between a cancerous condition and a non-cancerous condition, or between two differently treated samples. Also, miRNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992, which are hereby incorporated in their entirety for all purposes.

In addition to the use of arrays and microarrays, it is contemplated that a number of difference assays could be employed to analyze miRNAs, their activities, and their effects. Such assays include, but are not limited to, nucleic amplification, polymerase chain reaction, quantitative PCR, RT-PCR, in situ hybridization, digital PCR, dd PCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seg (Tagged-Amplicon deep sequencing), PAP (Pyrophosphorolysis-activation polymerization), next generation RNA sequencing, northern hybridization, hybridization protection assay (HPA)(GenProbe), branched DNA (bDNA) assay (Chiron), rolling circle amplification (RCA), single molecule hybridization detection (US Genomics), Invader assay (ThirdWave Technologies), and/or Bridge Ligation Assay (Genaco).

In certain aspects, the methods and compositions described herein may include the use of exosomes that have been isolated or enriched from the patient. Exosomes may be cell-derived vesicles that are present in many and perhaps all biological fluids, including blood, urine, and cultured medium of cell cultures. The diameter of exosomes may be between 30 and 100 nm, which is larger than LDL, but much smaller than for example red blood cells. In certain aspects, the diameter of exosomes may be at least about, about, or at most about 1, 5, 10, 20, 30, 31, 32, 33, 34, 35, 36, 37, 38, 39, 40, 41, 42, 43, 44, 45, 46, 47, 48, 49, 50, 100, 500, 1,000 nm or any range or value derivable therefrom.

Exosomes are either released from the cell when multivesicular bodies fuse with the plasma membrane or they are released directly from the plasma membrane. It is becoming increasingly clear that exosomes have specialized functions and play a key role in, for example, coagulation, intercellular signaling, and waste management. Consequently, there is a growing interest in the clinical applications of exosomes. Exosomes can be used for prognosis, therapy, and biomarkers for health and disease.

Any known methods in the art can be used to isolate or enrich exosomes. For example, ultracentrifugation, microfiltration, size-exclusion chromatography, or a gradient can be used to isolate exosomes. Antibody-based methods may be used to isolate antigen-specific exosomes, and can be used in combination with other separation methods.

VII. Pharmaceutical Compositions

In certain aspects, the compositions or agents for use in the methods, such as chemotherapeutic agents or miR-320e inhibitors, are suitably contained in a pharmaceutically acceptable carrier. The carrier is non-toxic, biocompatible and is selected so as not to detrimentally affect the biological activity of the agent. The agents in some aspects may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration.

Certain aspects also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents described herein. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VIII. Kits

Certain aspects also concern kits containing compositions described herein or compositions to implement methods described herein. In some embodiments, kits can be used to evaluate one or more miRNA molecules. In certain embodiments, a kit contains about, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more miRNA probes, synthetic miRNA molecules or miRNA inhibitors, or any value or range and combination derivable therein. In some embodiments, there are kits for evaluating miRNA activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using miRNA probes, synthetic miRNAs, non-synthetic miRNAs, and/or miRNA inhibitors described herein for prognostic or diagnostic applications are included in certain aspects. Specifically contemplated are any such molecules corresponding to any miRNA identified herein.

In certain aspects, negative and/or positive control synthetic miRNAs and/or miRNA inhibitors are included in some kit embodiments. The control molecules can be used to verify transfection efficiency and/or control for transfection-induced changes in cells.

It is contemplated that any method or composition described herein can be implemented with respect to any other method or composition described herein and that different embodiments may be combined. It is specifically contemplated that any methods and compositions discussed herein with respect to miRNA molecules or miRNA may be implemented with respect to synthetic miRNAs to the extent the synthetic miRNA is exposed to the proper conditions to allow it to become a mature miRNA under physiological circumstances. Any embodiment involving specific miR-NAs by name is contemplated also to cover embodiments involving miRNAs whose sequences are at least 80, 81, 82, 83, 84, 85, 86, 87, 88, 89, 90, 91, 92, 93, 94, 95, 96, 97, 98, 99% identical to the mature sequence of the specified miRNA.

Certain embodiments include kits for analysis of a sample by assessing miRNA profile for a sample comprising, in suitable container means, two or more miRNA probes, wherein the miRNA probes detect one or more of the miRNA identified herein. The kit can further comprise reagents for labeling miRNA in the sample. The kit may also include labeling reagents, including at least one of amine-modified nucleotide, poly(A) polymerase, and poly(A) polymerase buffer. Labeling reagents can include an amine-reactive dye.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 miR-320e as a Novel Biomarker in Colorectal Cancer

Patients—Discovery Patient Cohort. A cohort of 100 stage III colon cancer tissue samples that included 50 patients with tumor recurrence, and 50 without recurrence within 3 years of treatment. These patients were enrolled as part of the NCCTG N0147, a phase III trial of FOLFOX alone or combined with cetuximab as adjuvant chemotherapy (Alberts, et al., 2012); however, the clinical specimens in this study were limited to the FOLFOX alone study arm. Median patient follow-up on this trial was 4.1 years. Of the 47 patients without tumor recurrence and 50 with recurrence from whom miRNA expression profiling was successfully obtained, 53.2% and 56% were treated with FOLFOX alone respectively. This study was approved by the Institutional Review Boards (IRB) of all participating centers, and a written informed consent was obtained from all patients. Data are summarized either as mean with 95% confidence intervals (CI) on the $\log_2$ scale, or these values were exponentiated to generate fold-change with a confidence interval.

Validation Patient Cohort. This group included a total of 237 CRC patients (65 stage II, 102 stage III, and 70 stage IV) that were enrolled as part of a clinical trial conducted at the Hospital Clinic, Barcelona, Spain. Patients in this clinical trial were enrolled between 1996 and 2008, and the median follow-up was 4.7 years in patients that were alive at last follow-up, and 3.5 years for all patients. All stage II and III patients were treated with 5-FU-based adjuvant chemotherapy following resection of the primary tumor; all stage IV patients were treated with 5-FU and oxaliplatin (Takahashi, et al., 2012). Normal colonic mucosa (n=20) from healthy individuals was obtained from the Pathology Department of the Hospital Clinic of Barcelona and included as controls. This study was approved by the Institutional Review Board (IRB) of Hospital Clinic, Barcelona, Spain, and a written informed consent was obtained from all patients.

RNA extraction. Total RNA including the miRNA fraction was extracted from formalin-fixed paraffin-embedded (FFPE) tissues using the RecoverAll Total Nucleic Acid Isolation Kit (Ambion, Inc., Austin, Tex., USA) according to the manufacturer's protocol.

Array methodology. Analysis was performed using the Affymetrix GeneChip® miRNA 2.0 Array (Santa Clara, Calif.). Samples were labeled using the Genisphere FlashTag Biotin HSR kit (Hatfield, Pa.). Briefly, one microgram of total RNA from FFPE samples was incubated with ATP and Poly A polymerase to add a 3' polyA tail. A ligation reaction was then performed to covalently attach to the miRNA population a multiple-biotin molecule containing a 3DNA dendrimer. Labeled samples were subsequently processed according to manufacturer's instructions. After hybridization for 16 h at 48° C., the arrays were washed and stained in an Affymetrix Fluidics station 450, then scanned in an Affymetrix 3000 7G scanner. The 1,105 human miRNA transcripts that are interrogated on Affymetrix GeneChip® miRNA 2.0 Array were analyzed.

MiRNA expression microarrays. MiRNA microarray expression profiling analysis included interrogation of ~2,221 miRNAs, using the Affymetrix GeneChip® miRNA 2.0 Arrays (Santa Clara, Calif.). Each sample was labeled using the Genisphere FlashTag Biotin HSR kit (Hatfield, Pa.). Briefly, one microgram of total RNA was incubated with ATP and Poly-A-polymerase to add a 3'-polyA tail. A ligation reaction was then performed to covalently attach to the miRNA population a multiple-biotin molecule containing a 3'-DNA dendrimer. Labeled samples were subsequently processed according to manufacturer's instructions. Following hybridization for 16 h at 48° C., the arrays were washed and stained in an Affymetrix Fluidics station 450, scanned using an Affymetrix 3000 7G scanner, and the expression changes between cases and controls were analyzed.

Quantification of miRNA expression by real-time RT-PCR. Expression of miR-320e in the validation patient cohort was performed utilizing the Taqman reverse transcription-PCR (qRT-PCR) method with the TaqMan miRNA expression assay (Applied Biosystems Inc., Foster City, Calif.) in a StepOnePlus™ Real-Time PCR System (Applied Biosystems). All the experiments were done in duplicate. Results were expressed as $2^{-\Delta Ct}$ and normalized to miR-16. To keep consistent measurements throughout all plates, two independent RNA cell line samples were loaded as internal controls in each PCR run, and the results from each plate were normalized according to data obtained from these internal controls.

Statistical analysis. The quality of the raw Affymetrix miRNA data was assessed using boxplots and residual MVA plots for each subject pre- and post-normalization (Eckel, et al., 2005). Per-probe and -patient distributions of detection calls were also examined, where signal intensities with detection p<0.06 were considered to be detected. The non-human probes were excluded prior to normalization, leaving 2,221 human miRNA transcripts for analyses. Data were analyzed on the $\log_2$ scale, and were normalized using quantile normalization (Bolstad, et al., 2003). Differential expression between tumors with and without recurrence within 3 years was performed via logistic regression by incorporating various variables: both unadjusted and adjusted individually for deficient DNA mismatch repair (dMMR) vs. proficient MMR (pMMR) status, presence/absence of a BRAT'$^{V600E}$ or KRAS mutation, right vs. left side, and metastatic regional lymph nodes <4 or >=4. FDR values were calculated, and the significance level was set at FDR q<0.05 (Storey & Tibshirani, 2003). Probes were filtered out of consideration if the standard deviation (SD) in cases and controls combined for a given probe was less than the $95^{th}$ percentile SD (0.164) for probes that were not detected in ≥45% of the samples.

Distributions in the validation cohort are presented as mean (SD) or median (range) depending on level of skewness in the data for continuous variables, or as counts (percentage) for categorical variables. Nonparametric tests (rank sum, Kruskal Wallace) were used to compare expression between groups. Kaplan Meier and Cox regression models were used to assess association with time to event outcomes that included overall survival (OS), defined as time from diagnosis to death, and disease free survival (DFS) defined as time from diagnosis to disease recurrence or death. Due to the scale of miR320e expression, hazard ratios are presented as the change in risk of a person at the $75^{th}$ percentile relative to a person at the $25^{th}$ percentile of miR-320e distribution. This can be interpreted as the increase in risk due to a patient moving from the middle of the bottom half of the miR-320e distribution to the middle of the top half of the distribution. Bootstrapping was used to calculate an optimism corrected c-index, analogous to the area under the receiver operating characteristic curve (Steyerberg, et al., 2011). A c-index of 0.5 denotes random predictions, whereas a c index of 1 denotes perfect predictions.

Discovery Patient Cohort. The initial cohort contained 50 patients that recurred within 3 years and 50 patients that did not recur within 3 years. Of these patients miRNA data were received on 50 of the patients that recurred within 3 years and 47 of the patients that did not recur within 3 years and all were deemed to be of good quality. The mean±SD age for these 97 patients was 57.3±11.8 and 46 (47.4%) were male. There were 47 (48.5%) tumors that were distal and 48 (49.5%) tumors that were proximal and 2(2.1%) that were both. All patients had TMN stage 3.

Of the 1,105 miRNA probes analyzed, two met the significance criteria with unadjusted analyses: hp_hsa-mir-518e_x_st and hsa-miR-320e_st, with p=3.22E−05 and 4.48E−05, respectively, and both with FDR q-value of 0.0497. miR-320e was up-regulated in cases versus controls; the mean level of miR-320e expression (mean±SD) in patients that recurred within 3 years was 8.066365±0.463103 vs. 7.716739±0.334095 in patients that did not recur within 3 years, which had a raw fold change of 1.27423 and unadjusted p-value of p<0.0001. mir-518e was one of 86 probes filtered out due to low standard deviation (and therefore high risk of false discovery).

Validation Patient Cohort. In the validation cohort of 237 CRC cases, the mean I SD age of the patients was 64±10 years of age and the majority of patients were male 141 (59.5%). Of the 237 tumors, 80 (33.7%) were located in the proximal colon, 144 (60.7%) were distal, and 13 (5.6%) were located in the rectum. Approximately 66 (27.8%) of the cases were stage II, 101 (42.6%) stage III, and stage IV in the remaining 70 (29.6%) of the tumors (Table 1).

TABLE 1

Characteristics of Clinical cohort patients
Table 1. Characteristics of Clinical patients

| Characteristics | No. (%) of Patients |
|---|---|
| Age, mean (SD) | 64 (10) |
| Gender, n(%) | Male, 141 (59.4) |
|  | Female, 96 (40.6) |
| TNM, n(%) | II, 66 (27.8) |
|  | III, 101 (42.6) |
|  | IV, 70 (29.6) |
| Location, n(%) | Left colon, 144 (60.7) |
|  | Right colon, 80 (33.7) |
| Grade, n(%) | Well, moderate, 140 (96.5) |
|  | Poor, 5 (3.5) |
| Mucinous, n(%) | Yes, 25 (16.3) |
|  | No, 125 (83.7) |
| Follow-up, mean(SD) | 1666 (896) | miR320e results were expressed as $2^{-\Delta Ct}$ and normalized to miR-16. The mean level of miR-320e expression (mean±SD) in primary colorectal tumor tissues was almost ten-fold higher than in normal colonic mucosa (0.0052±0.0046 vs 0.00067±0.00076; p<0.0001). They are 2−ΔCt expression values from RT-qPCR method, corrected by internal plate controls, the standard method for miRNA expression. As is a semi-quantitative method, miR320e expression was compared with a normalizer (miR16), and a reasonable difference between miR320 and miR16 Ct values (around 6-8 Cts) was found.

Figure 1B:
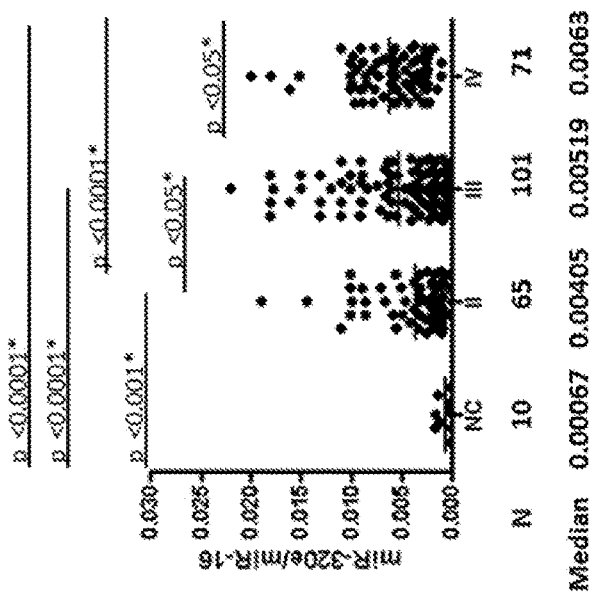
Figures 1C, 1D, 1E:
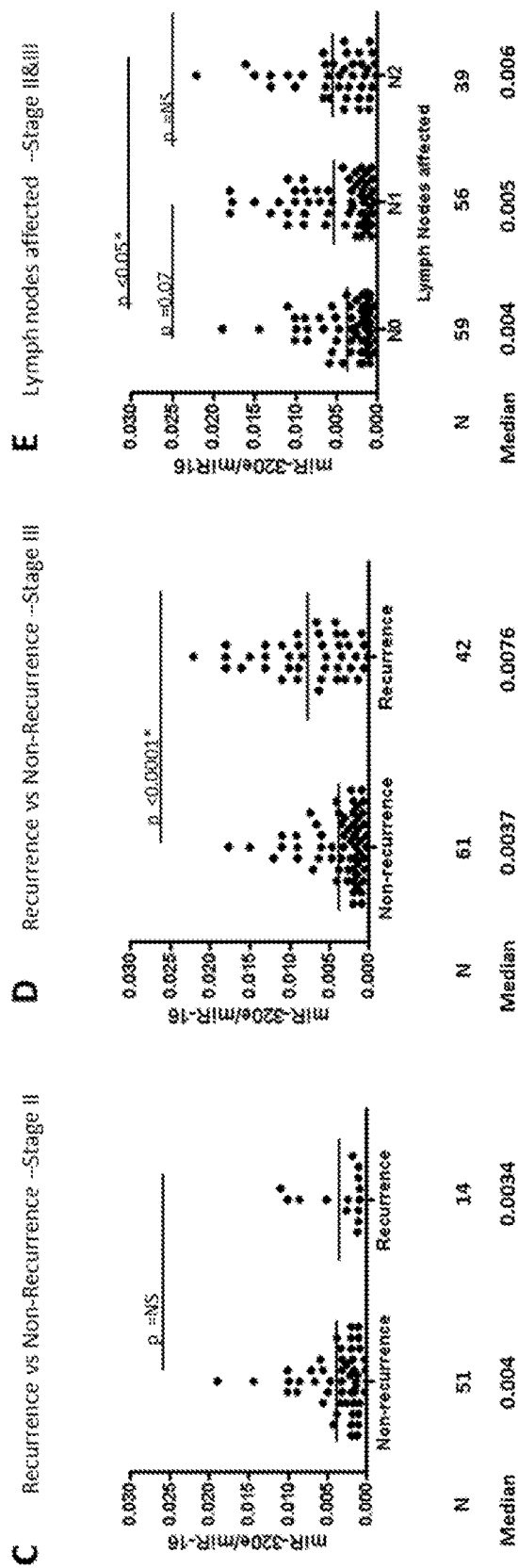

There was a trend toward gradual increasing of miR-320e expression with advancing stage of the CRCs, specifically, a significant miR-320e up-regulation was shown in CRC patients with lymph node (stage III) (0.0053±0.0049 vs 0.004±0.0047; p<0.05) or distant metastasis (IV) (0.0062±0.003 vs 0.004±0.0047; p<0.0001) compared to patients without (II). The results confirmed that miR-320e expression was up-regulated in primary tumors with stages II and III patients who had locoregional relapse and/or distant metastasis during follow-up compared to those without, and in patients with 4 or more nearby lymph nodes affected (N2) compared to those patients without any lymph node affected (TNM Stage II; p<0.05) (FIG. 1). These results demonstrate the potential role of miR-320e in CRC progression and metastasis.

MiR-320e is frequently upregulated in CRC patients with recurrence to 5-FU based chemotherapy. The Discovery Phase: Systematic discovery for miRNA biomarkers was performed using Affymetrix microarrays in 100 stage III patients treated with 5-FU based adjuvant chemotherapy, during the course of NCCTG NO147 trial. High quality miRNA data was obtained on all but 3 patients without tumor recurrence at 3 years of follow-up. The median age (range) for these 97 patients was 59 (25-81) years, of which 46 (47.4%) were male. There were 48 (49.5%) primary tumors that were located in the distal colon and 49 (50.5%) tumors that were proximal (Table 2).

TABLE 2

Characteristics of patients in the discovery and validation cohorts

| Characteristics | Discovery Cohort N (%) | Validation Cohort N (%) |
|---|---|---|
| Age, median (range) | 59(25-81) | 65(32-82) |
| Gender, n(%) | Male, 51 (52.6) | Male, 141 (59.5) |
|  | Female, 46 (47.4) | Female, 96 (40.5) |
| TNM, n(%) | II, 0 (0) | II, 65 (27.4) |
|  | III, 97 (100) | III, 102 (43.0) |
|  | IV, 0 (0) | IV, 70 (29.5) |
| Location, n(%) | Left colon, 48 (49.5) | Left colon, 155 (65.4) |
|  | Right colon, 49 (50.5) | Right colon, 69 (29.1) |
| Grade, n(%) | Low (Grade 1-2) 68 (70.1) | Well, moderate, 140 (96.5) |
|  | High (Grade 3-4) 29 (29.9) | Poor, 5 (3.5) |
| Mucinous, n(%) | — | Yes, 25 (16.3) |
|  | — | No, 128 (83.7) |
| Follow-up in all patients, median (range) | 3.2 (range 0.35-7.1 years) | 4.4 years (range 0.24-14.4 years) |

Figure 3:
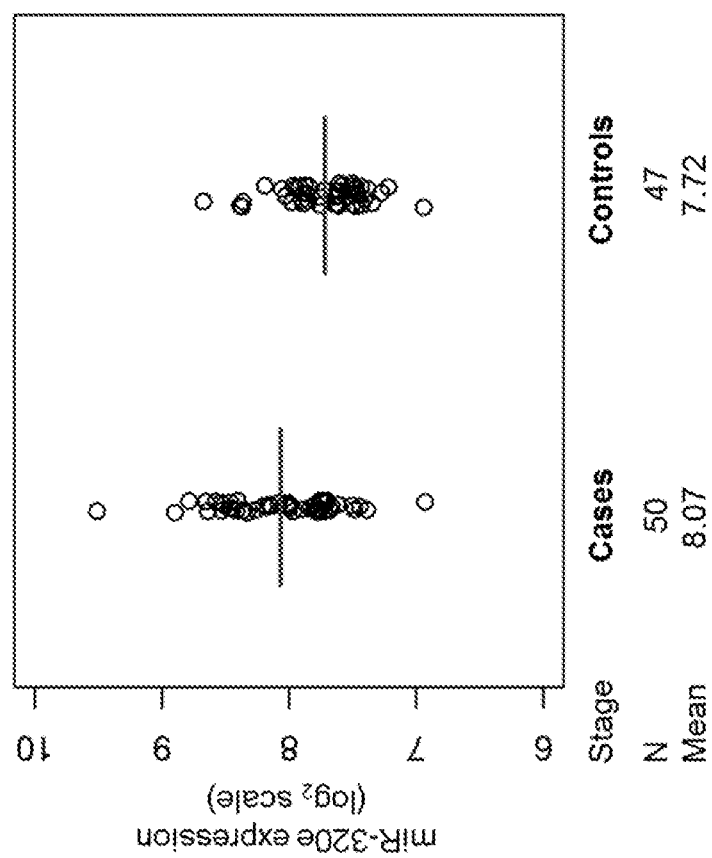
FIG. 3—MiR-320e expression in the discovery cohort. $Log_e$ normalized expression levels for miR-320e in stage III colorectal cancers treated with 5-FU based chemotherapy. Cases (patients with tumor recurrence) had significantly higher miR-320e expression compared to controls (patients without recurrence). The red line indicates median value for expression.

Of the 2,221 miRNA probes analyzed, one met statistical significance criteria with unadjusted analyses: miR-320e, with p<0.0001 and a corresponding FDR q-value of 0.0497. MiR-320e was up-regulated in cases with recurrence versus no recurrence (controls; FIG. 3). Specifically, the mean level of miR-320e expression (mean±SD) on the log2 scale in patients that recurred was 8.07±0.46 vs. 7.72±0.33 compared to patients without recurrence, resulting in a raw fold change of +1.27 fold. After adjusting for sidedness, the mutational status of BRAF and KRAS, and number of metastatic regional lymph nodes (< or ≥4), miR-320e expression was significantly higher in cases vs. controls (p=0.0003).

The Validation Phase: To further confirm the discovery phase results for miR-320e expression, validation of these data was performed in an independent cohort of 237 patients with stage II-IV CRC. The median (range) age of the patients was 65 (32-82) years, and of these 141 (59.5%) patients were male. Of the 237 CRCs, 69 (29.1%) were located in the proximal colon, 155(65.4%) were distal, and 13 (5.5%) were located in the rectum. Sixty-five (27.43%) of the cases were stage II, 102 (43.04%) stage III, and 70 (29.5%) were stage IV (Table 2).

Figures 4A, 4B:
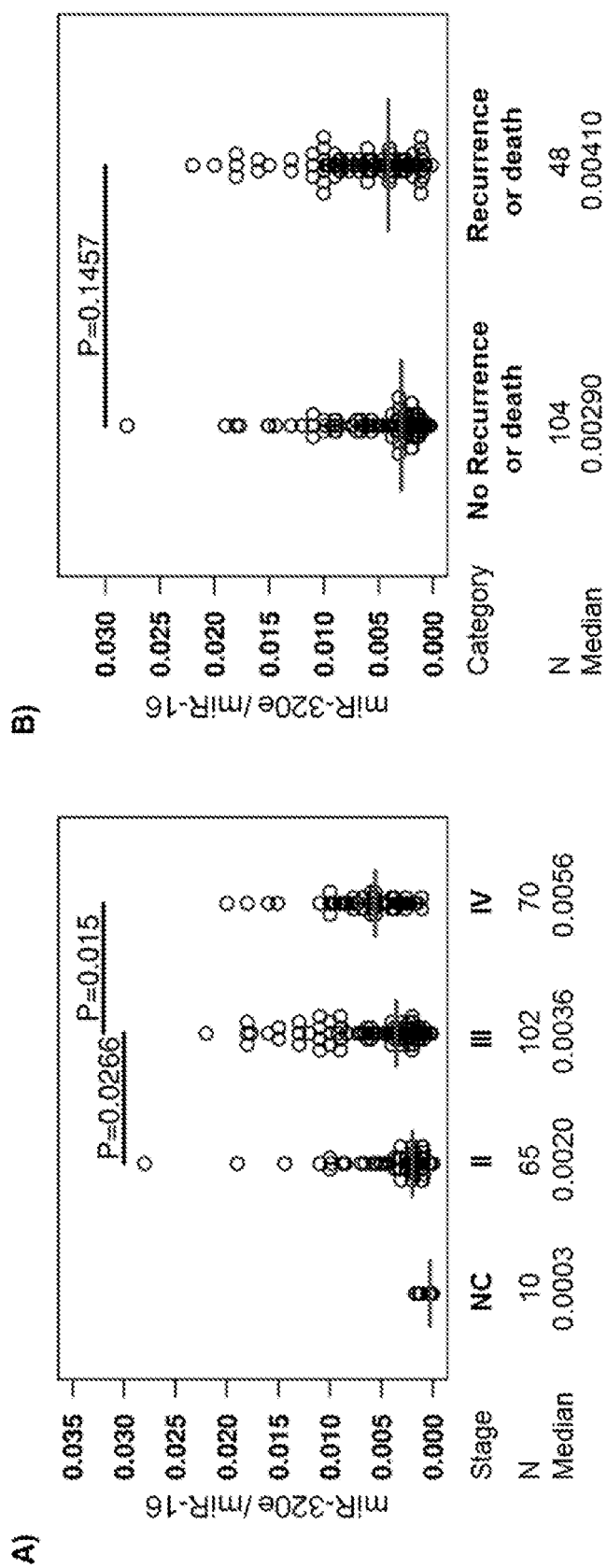
FIG. 4A-4B—MiR-320e expression in normal colonic mucosa and CRC tissues from the validation cohort. MiR-320e results were expressed as $2^{-\Delta Ct}$ and normalized to miR-16. A) Colonic mucosa vs. primary tumors—stage II-IV, miR-320e expression in colonic mucosa from healthy controls (NC), and in stage II, III and IV CRCs; the number of patients (N) and median expression (median) are listed below the graph. B) Recurrence or death within 3 years vs. Non-Recurrence or death within 3 years—Stage II & III, miR-320e expression; the number of patients (N) and median expression (median) are listed below the graph. The red line indicates median value for expression.

MiR320e results were expressed as $2^{-\Delta Ct}$ and normalized with the expression of miR-16. The median level of miR-320e expression in primary CRC tissues was almost thirteen-fold higher than in normal colonic mucosa [median (range): 0.000286 (0.0000238-0.0017000) vs. 0.0037 (0-0.028), p<0.0001)]. There was a gradual increasing trend for miR-320e expression with advancing tumor stage (FIG. 4A). Specifically, significant miR-320e up-regulation was found in CRC patients with lymph node metastases, i.e., stage III [0.00357 (0.00013-0.022) vs 0.00200 (0-0.028); p=0.0266] or with distant metastasis, i.e., stage IV [0.0056 (0.0011-0.02) vs 0.00200 (0-0.028); p<0.0001] compared to patients without regional or distant metastases, i.e., stage II.

Higher expression miR320e is associated with poor outcome in patients with stage II and III CRC. To determine the potential prognostic significance of miR-320e expression, Cox regression models were utilized with the miRNA expression levels considered as continuous variables. There were 167 stage II and III CRC patients in the validation cohort with sufficient data for these analyses. All of these patients were treated with 5-FU-based adjuvant chemotherapy for 6 months subsequent to tumor resection. Of these patients, 65 out of 167 (38.9%) were stage II and the remainder were stage III. Median follow-up for these patients was 4.4 years (range 0.24-14.4 years), and was 4.7 years for patients alive at last follow-up (range 0.69-14.4 years). The 2- and 5-year Kaplan-Meier DFS estimates were 78.32% (72.29, 84.84) and 63.96% (56.58, 72.30), respectively. The 2- and 5-year OS estimates were 91.57% (95% CI: 87.44, 95.89) and 78.52% (95% CI: 72.15, 85.46), respectively.

Figures 5A, 5B:
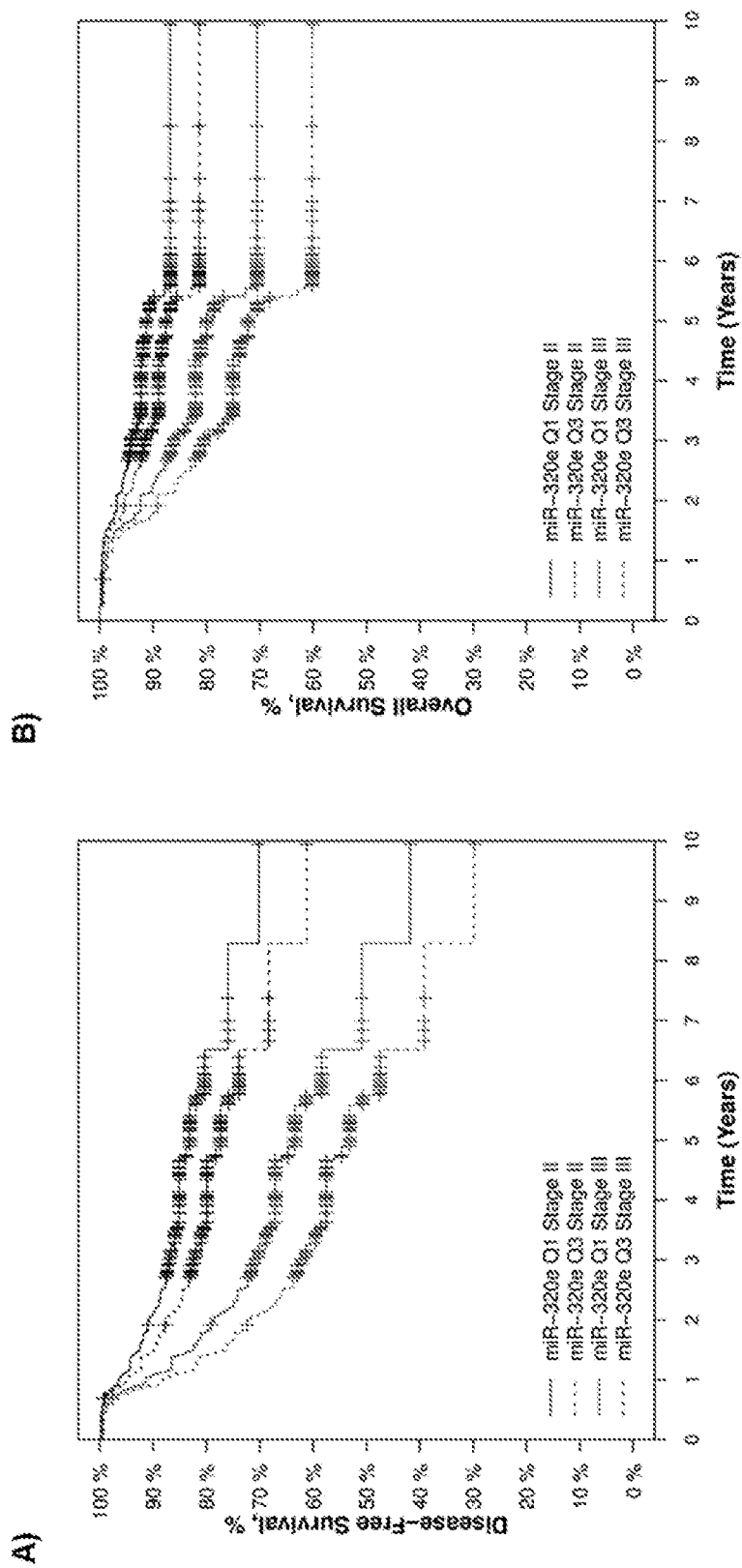
FIG. 5A-5B—Predicted DFS and OS Survival Functions. Predicted DFS A) and OS B) from the Cox regression model containing TNM stage, tumor location, and miR-320e expression to visualize the hazard ratios reported in Table 3. Tumor location was set to the left side for the figures. Stage II curves are blue; stage III curves are red. Q1 (solid line) denotes patients with miR-320e expression at the $25^{th}$ percentile, while Q3 (dashed line) denotes patients with miR-320e expression at the $75^{th}$ percentile. Thus, the curves represent survival functions for patients in the middle of the bottom half of the miR-320e distribution versus those in the middle of the top half of the miR-320e distribution.

Multivariate models were employed to interrogate the statistical significance of results in these 167 stage II/III patients, and to assess the association of miR-320e expression with DFS and OS, after adjusting for tumor location and TNM stage. After adjustment for TNM stage and tumor location in stage II and III patients, an increase of 0.0052 units of miR-320e expression (i.e., an increase from the $25^{th}$ percentile to the $75^{th}$ percentile of the miR-320e distribution) was associated with an increased hazard ratio for DFS (HR=1.39, 95% CI: 1.11-1.74, p=0.0036) and OS (HR=1.46, 95% CI: 1.11-1.91, p=0.0059; Table 3, FIG. 5). The optimism-corrected c-indices were 0.63 and 0.62 for DFS and OS, respectively.

TABLE 3

Multivariable analysis of the association between DFS or OS and miR-320e expression in stage II/III CRC patients, adjusting for tumor location and stage

| Variable | Multivariate Analysis Stage II & III | | | | |
|---|---|---|---|---|---|
|  | Event/Total | HR | 95% CI | p-value | c-index |
| Disease-Free Survival | | | | | |
| miR-320e (per 0.0052 units*) | 60/167 | 1.39 | 1.11-1.74 | 0.0036 | 0.63 |
| tumor location (proximal vs. distal) |  | 1.05 | 0.61-1.79 | 0.8606 |  |
| TNM (III vs. II) |  | 2.46 | 1.34-4.50 | 0.0035 |  |
| Overall Survival | | | | | |
| miR-320e (per 0.0052 units*) | 38/167 | 1.46 | 1.11-1.91 | 0.0059 | 0.62 |

TABLE 3-continued

Multivariable analysis of the association between DFS or OS and miR-320e expression in stage II/III CRC patients, adjusting for tumor location and stage

| Variable | Multivariate Analysis Stage II & III | | | | |
|---|---|---|---|---|---|
| | Event/Total | HR | 95% CI | p-value | c-index |
| tumor location (proximal vs. distal) | | 1.08 | 0.55-2.11 | 0.8251 | |
| TNM (III vs. II) | | 2.46 | 1.12-5.37 | 0.0244 | |

HR, Hazard Ratio; CI, Confidence Interval;
*This is the IQR, representing an increase from the 25$^{th}$ percentile to the 75$^{th}$ percentile of the miR-320e distribution.

When categorizing stage II/III the patients into those who had recurred or died within 3 years vs those who were recurrence-free and alive at ≥3 years of follow-up, miR-320e was not significantly different between these groups (0.00410(0.00013-0.02200) vs 0.00290 (0.00023-0.02800)), p=0.1457; FIG. 4B). However, when the cohort was restricted to stage III patients, the level of miR-320e expression was found to be significantly different between patients who had recurred or died within 3 years vs. those who were alive and recurrence free after 3 or more years of follow-up (0.00578 (0.00013-0.02200) vs 0.00260 (0.00025-0.01800), p=0.0132).

To test the prognostic significance of miR-320e expression, samples were categorized into two groups based on the expression levels in primary tumors, and the dose-response relationship between the rate of expression and event-free survival examined by ROC curve analysis. All stage II and III patients (167) used in this analysis were treated with 5-FU-based adjuvant chemotherapy for 6 months subsequent to tumor resection.

A total of 167 stage II-III patients from the validation cohort were included, 66 out of 167 (39.5%) were stage II and the rest stage III. From those, 72 CRC patients were classified as miR-320e high expression tumors (42.8%) and the rest were classified as low expression tumors. Median follow-up for these patients was 1640 days (4.5 years; range 88-5630 days). A total of 38 out of the 167 patients died during follow-up (22.6%) and the median follow-up time for this group was 1060±901 days (2.9±2.5 years).

Of these 38 patients, 79% (30/38) died due to tumor progression, and the remaining 21% (8/38) patients died from other causes. Of those patients still alive, fifty-five patients (32.9%) had tumor recurrence; all 55 with distant metastasis and 17 of these patients (30.9%) had locoregional recurrence as well. These recurrences were seen at a median of 742±604 days (2±1.6 years) after surgery.

Figures 2A, 2B:
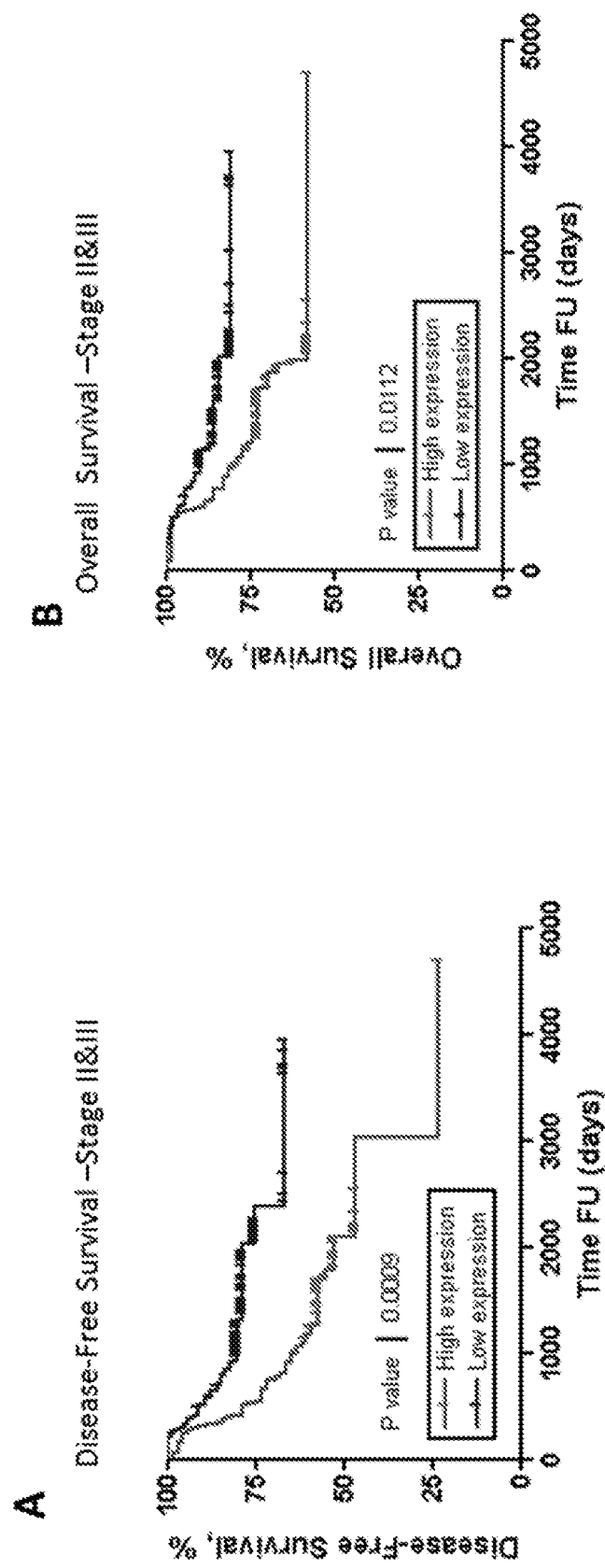
FIG. 2A-2D—Survival analysis in stage II/III patients treated with 5-FU-based chemotherapy. A. Disease-Free Survival of patients with stage II and III disease, according to miR-320e expression status (High expression N=72 (43.1%); Low expression N=95 (56.9%)) (HR=2.44; 95% CI, =1.46-4.31). B. Overall Survival of patients with stage II and III disease, according to miR-320e expression status (High expression N=72 (43.1%); Low expression N=95 (56.9%)) (HR=2.38; 95% CI, =1.23-4.56). C. Disease-Free Survival of stage II CRC patients (High expression N=23 (33.8%); Low expression N=45 (66.2%)) (HR=0.78; 95% CI, =0.26-2.39). D. Disease-Free Survival of stage III CRC patients (High expression N=51 (50%); Low expression N=51 (51%)) (HR=3.46; 95% CI, =1.77-6.11)
Figures 2C, 2D:
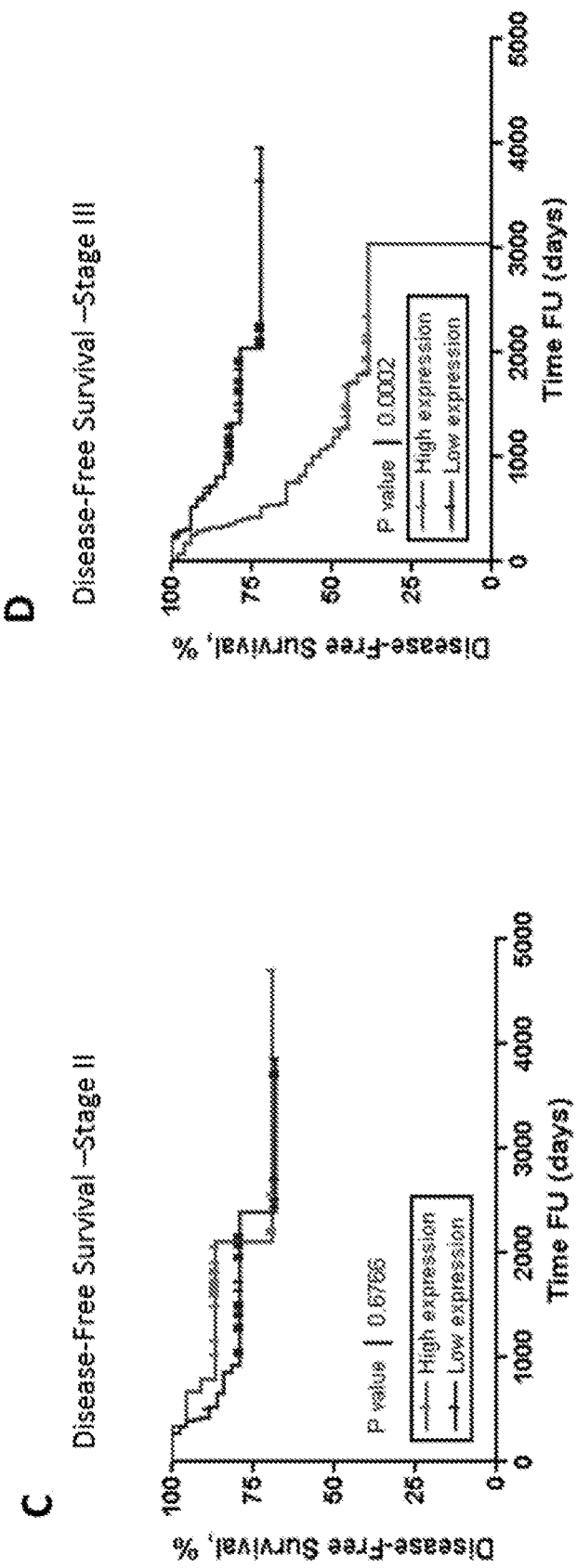

High expression of miR-320e was a predictor for poor prognosis in stage II-III CRC patients, and affected survival DFS (High expression (mean±SD) DFS: 1307±818; Low expression: 1500±816; p=0.0009). This positive relationship remained when separate stage III patients were studied (High expression N=51 (50%); Low expression N=51 (51%); p=0.0002) but not for stage II patients alone (High expression N=23 (33.8%); Low expression N=45 (66.2%)); p=0.67) (FIG. 2).Furthermore, high levels of miR-320e expression was the only statistical significant risk factor for stage III CRCs, after adjusting for other prognostic factors as age, gender, tumor location, tumor size, grade of differentiation or mucinous histology in the multivariate Cox regression analysis (HR=2.34, 95% CI: 1-1.5, p=0.03) (Table 4).

TABLE 4

Multivariate analysis of miR-320e expression and DFS in stage II/III CRC patients.

| | Multivariate | | | | | |
|---|---|---|---|---|---|---|
| | Stage II & III | | | Stage III | | |
| Variables | HR | 95% CI | p-value | HR | 95% CI | p-value |
| Age (<67 vs >67) years | — | — | — | — | — | — |
| Gender (Male vs Female) | — | — | — | — | — | — |
| Tumor location (Distal vs Proximal) | — | — | — | — | — | — |
| Tumor size (>45 mm(median)) vs <45 mm | — | — | — | — | — | — |
| Grade off Differentiation (well, moderate vs poor) | — | — | — | — | — | — |
| Mucinous (Positive vs Negative) | — | — | — | — | — | — |
| Lymph node (Positive vs Negative) | 2.35 | 1.09-5.05 | 0.03 | — | — | — |
| miR-320e (High vs Low expression) | 1.88 | 0.99-3.56 | 0.05 | 2.34 | 1.1-5 | 0.03 |

Abbreviations:
HR, Hazard Ratio;
CI, Confidence Interval.

Next, the clinicopathological features associated with tumor miR-320e expression levels was investigated. The variables included in this analysis were age, gender, tumor location, tumor size, grade of differentiation, mucinous histology, and lymph node metastasis. Tumor location and TNM stage were not associated with the expression status of miR-320e. Interestingly, miR-320e was positively associated with tumor size (p=0.11) and lymph node metastasis (p=0.06); however, these associations were not statistically significant (Table 5).

TABLE 5 miR-320e expression status and clinicopathologic characteristics of stage II & III CRC patients

| Characteristics Stages II-III | | High Expression n = 72 (43.1%) | Low Expression n = 95(56.9%) | P-value |
|---|---|---|---|---|
| Age, Mean (SD) | | 66 (8.1) | 64 (10) | NS† |
| Gender | Male | 42 (58) | 53 (58.8) | NS* |
| N (%) | Female | 30 (42) | 42 (41.2) | |
| Tumor Location | Distal | 51 (70.8) | 62 (64.6) | NS* |
| N (%) | Proximal | 21 (29.2) | 34 (35.4) | |
| Tumor Size | <45 mm | 26 (39) | 46 (52.3) | 0.11 |
| N (%) | >45 mm | 40 (61) | 42 (47.7) | |
| Grade off | G0, G1 | 62 (46.8) | 78 (96.3) | NS* |

TABLE 5-continued miR-320e expression status and clinicopathologic characteristics of stage II & III CRC patients

| Characteristics Stages II-III | | High Expression n = 72 (43.1%) | Low Expression n = 95(56.9%) | P-value |
|---|---|---|---|---|
| Differentiation N (%) | G2 | 2 (3.2) | 3 (3.7) | |
| Mucinous N (%) | Yes | 11 (16.9) | 14 (15.9) | NS* |
| | No | 54 (83.1) | 74 (84.1) | |
| Lymph Node Metastasis N (%) | Yes | 46 (69.6) | 48 (59.5) | 0.06 |
| | No | 20 (30.4) | 40 (45.5) | |

†Evaluated with Student's t test
*Evaluated at X2 test of Fisher's exact test

High miR-320e expression associated with advancing CRC stage. Analysis of the clinicopathological features associated with tumor miR-320e expression levels was also investigated. The variables included in this analysis were age, gender, tumor location, tumor size, tumor grade, mucinous, histology, stage, and lymph node metastasis. TNM stage was found to be significantly associated with expression level of miR-320e (p=0.0266). Age was not significantly correlated with miR-320e expression levels (r=0.0626 p=0.4220). Neither tumor location nor lymph node metastasis were significantly associated with the expression level of miR-320e (Table 6). Interestingly, there was a trend toward a positive association between miR-320e and tumor size (p=0.1047) and with lymph node metastasis (p=0.0626); however, these associations were not statistically significant at the 5% level (Table 6).

TABLE 6 miR-320e expression levels and clinico-pathologic characteristics of stage II&III CRC patients

| Characteristics Stages II-III | | Patient Number (Percent) | MiR-320e expression Median (Range) | P-value |
|---|---|---|---|---|
| Age | | 67 (32-82)# | | |
| Gender* | Male | 96 (57.5%) | 0.00305 (0-0.022) | 0.9638 |
| | Female | 71 (42.5%) | 0.00300 (0.00033, 0.028) | |
| Tumor Location* | Distal | 113 (67.7%) | 0.00310 (0.00023-0.022) | 0.3618 |
| | Proximal | 54 (32.3%) | 0.00225 (0-0.028) | |
| Tumor Size* | <45 mm | 72 (46.8%) | 0.0025 (0.00013-0.028) | 0.1047 |
| | >45 mm | 82 (53.2%) | 0.00337 (0-0.019) | |
| Tumor Grade* | G1, G2 | 140 (96.6%) | 0.00305 (0.00013-0.028) | 0.1843 |
| | G3 | 5 (3.4%) | 0.00090 (0.00067-0.009) | |
| Mucinous* | Yes | 25 (16.3%) | 0.0033 (0-0.018) | 0.9469 |
| | No | 128 (83.7%) | 0.00285 (0.00013-0.028) | |
| Lymph Node Metastasis* | Yes | 95 (61.7%) | 0.0034 (0.00013-0.022) | 0.0626 |
| | No | 59 (38.3%) | 0.00200 (0-0.028) | |
| TNM | 2 | 65 (38.9%) | 0.002 (0-0.028) | 0.0266 |
| | 3 | 102 (61.1%) | 0.00357 (0.00013-0.022) | |

*Evaluated using Wilcoxon Rank Sum test;
Age, is represented as Median (range)

Example 2

Exosomes

Circulating cell-free nucleic acids have been reported as promising biomarkers for various types of human cancers, including colorectal cancer (CRC). However, these biomarkers generally lack disease and/or organ specificity. Exosome is a small membrane vesicle which contains nucleic acids such as microRNA (miRNA), long non-coding RNA (lncRNA), mRNA and DNA, and is involved in cell-to-cell communication. A marker known to be expressed specifically in colon, gastric and pancreatic cancer cells can be used to extract cancer-specific exosomes followed by miR-320 expression determination. For example, it is shown that A33-positive exosome can be isolated by immunoprecipitation using human A33 antibody.

Serum samples from patients with colorectal neoplasms and healthy controls were utilized. Total exosomes were isolated using the Total Exosome Isolation (from serum) kit (Invitrogen). Exosomes positive for A33 antigen were immunoprecipitated from total exosome using A33 antibody. Thereafter, total RNA including small RNA was extracted from A33-positive exosomes using the miRNeasy Serum/Plasma Kit (Qiagen). Expression levels of biomarker miRNAs (miR-21, miR-29a and miR-125b) in A33-positive exosomes were measured by real-time RT-PCR. Culture media of various types of cancer cell lines were used to test the specificity of A33-positive exosomes.

Biomarker miRNAs were detectable in A33-positive exosomes isolated from human serum samples. Importantly, levels of miR-21 in A33-positive exosomes were significantly higher in patients with colorectal neoplasms than in healthy controls.

Therefore, expression levels of biomarker miR-320e in A33-positive exosomes can be measured by real-time RT-PCR in A33-positive circulating exosomes.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications

REFERENCES

The following references, to the extent that they provide exemplary procedural or other details supplementary to those set forth herein, are specifically incorporated herein by reference.

Akao, et al., *Cancer Lett.* 300:197-204, 2011.
Alberts, et al., *Jama.* 307:1383-93, 2012.
Baek, et al., *Nature.* 455:64-71, 2008.
Banerjee, et al., *Genes Chromosomes Cancer.* 46:852-60, 2007.
Bertagnolli, et al., *J Clin Oncol.* 29:3153-62, 2011.
Beukers, et al., *J Urol.* 190:311-6, 2013.
Bluemn, et al., *Mol Cancer Res.* 11:568-78, 2013.
Bolstad, et al., *Bioinformatics.* 19:185-93, 2003.
Borralho, et al., *Febs J.* 276:6689-700, 2009.
Botti, et al., *Proc Natl Acad Sci USA.* 108:13710-5, 2011.
Boyer, et al., *Cancer Res.* 66:2765-77, 2006.
Bronisz, et al., *Nat Cell Biol.* 14:159-67, 2011.
Calin & Croce, *Nat Rev Cancer.* 6:857-66, 2006.
Eckel, et al., *Bioinformatics.* 21:1078-83, 2005.
Fournier, et al., *EMBO Mol Med.* 2:159-71, 2010.
Goff, et al., *PLoS One.* 4:e7192, 2009.
Goldberg, et al., *J Clin Oncol.* 22:23-30, 2004.
Hsieh, et al., *Carcinogenesis.* 34:530-8, 2013.
Kagan, et al., *Oncogene.* 11:2121-6, 1995.
Kim, et al., *Proc Natl Acad Sci USA.* 105:16230-5, 2008.
Kopetz, et al., *Oncology.* 22:260-70; discussion 270, 273, 275, 2008.
Kurokawa, et al., *J Gastroenterol.* 47:883-95, 2012.
Laudadio, et al., *Gastroenterology.* 142:119-29, 2012.
Lee, et al, *Pancreatology.* 9:293-301, 2009.
Liu, et al., *Mol Cancer Ther.* 9:1080-91, 2010.
Lujambio, et al., *Proc Natl Acad Sci USA.* 105:13556-61, 2008.
Mina & Sledge, *Nat Rev Clin Oncol.* 8:325-32, 2011.
Nairismagi, et al., *Oncogene.* 31:4960-6, 2012.
Nicoloso, et al., *Nat Rev Cancer.* 9:293-302, 2009.
Nishida, et al., *Ann Surg Oncol.* 19:3065-71, 2012.
O'Connor, et al., *J Clin Oncol.* 29:3381-8, 2011.
Onodera, et al., *J Cell Biol.* 197:983-96, 2012.
Schepeler, et al., *Cancer Res.* 68:6416-24, 2008.
Schetter, et al., *Jama.* 299:425-36, 2008.
Smith, et al., *CA Cancer J Clin.* 60:99-119, 2010.
Spizzo, et al., *Cell.* 137:586-586.e1, 2009.
Stark, et al., *PLoS One.* 5:e9685, 2010.
Storey & Tibshirani, *Proc Natl Acad Sci USA.* 100:9440-5, 2003.
Takahashi, et al., *PLoS One.* 7:e46684, 2012.
Tomimaru, et al., *Br J Cancer.* 103:1617-26, 2010.
Yang, et al., *Proc Natl Acad Sci USA.* 110:2312-7, 2013.
Zhou, et al., *J Biol Chem.* 285:21496-507, 2010.

---

---

What is claimed is:

1. A method for treating colorectal cancer in a patient, the method comprising:
administering a treatment comprising a thymidylate synthase inhibitor to a patient wherein a colon cancer tissue sample from the patient had been determined to have a first expression level of miR-320e that was less than a reference expression level of miR-320e determined in recurrent colon cancer tissue samples or administering a cancer treatment excluding the thymidylate synthase inhibitor to a patient determined to have at least about the same first expression level of miR-320e in colon cancer tissues from the patient relative to the reference expression level of miR-320e in recurrent colon cancer tissue samples.

2. The method of claim 1, wherein the method further comprises determining the first miR-320e expression level in the patient.

3. The method of claim 1, where the method further comprises obtaining a tissue sample from the patient.

4. The method of claim 1, wherein the colon cancer tissues comprise fresh tissues, frozen tissues, preserved tissues, formalin-fixed tissues, paraffin-embedded (FFPE) tissues, or tissues from a fine needle aspirate.

5. The method of claim 1, wherein the method comprises isolating and/or assaying nucleic acids in a tissue sample from the patient.

6. The method of claim 5, wherein assaying nucleic acids comprises the use of a microarray, PCR, digital PCR, digital droplet PCR, direct digital detection, BEAMing, Amplification Refractory Mutation Systems, RNA-Seq, Tagged-Amplicon deep sequencing, pyrophosphorolysis-activation polymerization, RT-PCR, in situ hybridization, northern hybridization, hybridization protection assay, branched DNA assay, rolling circle amplification, single molecule hybridization detection, Invader assay, Bridge Ligation Assay, next generation RNA sequencing, or a combination thereof.

7. The method of claim 1, further comprising recording the patient's and the reference miR-320e expression levels in a tangible medium.

8. The method of claim 1, further comprising reporting the patient's and the reference expression levels to the patient, a health care payer, a physician, an insurance agent, or an electronic system.

9. The method of claim 1, wherein the cancer is stage II or III colorectal cancer.

10. The method of claim 1, wherein the cancer is stage IV colorectal cancer.

11. The method of claim 1, wherein the thymidylate synthase inhibitor comprises a pyrimidine analog.

12. The method of claim 1, wherein the treatment comprising a thymidylate synthase inhibitor further comprises a platinum-based antineoplastic.

13. The method claim 1, wherein the thymidylate synthase inhibitor comprises 5fluorouracil (5-FU).

14. The method of claim 1, wherein the first expression level of miR-320e was determined in the patient while the patient was undergoing a current colorectal cancer treatment regimen comprising a thymidylate synthase inhibitor or wherein the level of miR-320e was determined in the patient after the patient completed a treatment regimen comprising a thymidylate synthase inhibitor.

15. The method claim 1, further comprising selecting a treatment, wherein the treatment comprises oxaliplatin.

16. The method of claim 12, wherein the platinum-based antineoplastic comprises oxaliplatin.

17. The method of claim 1, wherein the colon cancer tissues from the patient or reference comprise tissues from a biopsy or resection of a colon cancer tumor.

* * * * *